(12) United States Patent
Hunt et al.

(10) Patent No.: US 8,167,914 B1
(45) Date of Patent: May 1, 2012

(54) LOCKING INSERT FOR SPINE STABILIZATION AND METHOD OF USE

(75) Inventors: Wesley Hunt, Austin, TX (US); H. Kim Le, Houston, TX (US); Alex Chang, Lake Jackson, TX (US); Anwaar Qadir, Cleveland, OH (US)

(73) Assignee: Zimmer Spine, Inc., Minneapolis, MN (US)

( * ) Notice: Subject to any disclaimer, the term of this patent is extended or adjusted under 35 U.S.C. 154(b) by 791 days.

(21) Appl. No.: 12/174,438

(22) Filed: Jul. 16, 2008

(51) Int. Cl.
*A61B 17/70* (2006.01)

(52) U.S. Cl. ...................................................... 606/272

(58) Field of Classification Search .... 623/17.11–17.16; 606/256, 267, 270, 278, 302
See application file for complete search history.

(56) References Cited

U.S. PATENT DOCUMENTS

| | | | |
|---|---|---|---|
| 4,773,402 A | 9/1988 | Asher et al. |
| 5,282,863 A | 2/1994 | Burton |
| 5,549,608 A | 8/1996 | Errico et al. |
| 5,683,392 A | 11/1997 | Richelsoph et al. |
| 5,702,393 A | 12/1997 | Pfaifer |
| 5,728,098 A | 3/1998 | Sherman et al. |
| 5,954,725 A | 9/1999 | Sherman et al. |
| 5,964,760 A | 10/1999 | Richelsoph |
| 5,989,250 A | 11/1999 | Wagner et al. |
| 5,997,539 A | 12/1999 | Errico et al. |
| 6,132,430 A | 10/2000 | Wagner |
| 6,132,434 A | 10/2000 | Shermann et al. |
| 6,171,311 B1 | 1/2001 | Richelsoph |
| 6,187,005 B1 | 2/2001 | Brace et al. |
| 6,416,515 B1 | 7/2002 | Wagner |
| 6,454,773 B1 | 9/2002 | Sherman et al. |
| 6,485,491 B1 | 11/2002 | Farris et al. |
| 6,562,040 B1 | 5/2003 | Wagner |
| 6,565,566 B1 | 5/2003 | Wagner et al. |
| 6,565,567 B1 | 5/2003 | Haider |

(Continued)

FOREIGN PATENT DOCUMENTS

WO    WO 2008013539 A2    1/2008

OTHER PUBLICATIONS

Office Action issued in U.S. Appl. No. 12/174,484, mailed Jun. 21, 2011, 14 pages.

(Continued)

*Primary Examiner* — David Isabella
*Assistant Examiner* — Ann Schillinger
(74) *Attorney, Agent, or Firm* — Seager Tufte & Wickhem LLC

(57) ABSTRACT

A spine stabilization system having collars, resilient inserts and pins for coupling a rod to bone fasteners. A bone fastener may be advanced into a vertebral body. A first collar having a set of deflectable arms and a channel in a first end and an opening in the second end recessing to form a cavity may be positioned with the head of the bone fastener in the cavity. A rod may be advanced into the channel in the first end of each collar. The deflectable arms may have a set of recessed portions. The recessed portions may have an angular or arcuate profile. A resilient insert may be advanced into the collar and positioned in the recessed portions, with the bottom surface of the resilient insert in contact with the rod. A pin may be inserted in the resilient insert to inhibit removal of the resilient insert.

7 Claims, 5 Drawing Sheets

U.S. PATENT DOCUMENTS

| | | |
|---|---|---|
| 6,595,992 B1 | 7/2003 | Wagner |
| 6,613,050 B1 | 9/2003 | Wagner et al. |
| 6,660,005 B2 | 12/2003 | Toyama et al. |
| 6,783,528 B2 | 8/2004 | Vincent-Prestigiacomo |
| 6,837,889 B2 | 1/2005 | Shluzas |
| 6,843,791 B2 * | 1/2005 | Serhan .................... 606/272 |
| 6,866,664 B2 | 3/2005 | Schär et al. |
| 6,918,911 B2 | 7/2005 | Biedermann et al. |
| 7,022,122 B2 | 4/2006 | Amrein et al. |
| 7,090,674 B2 | 8/2006 | Doubler et al. |
| 7,276,069 B2 | 10/2007 | Biedermann et al. |
| 7,303,563 B2 | 12/2007 | Poyner et al. |
| 7,320,555 B2 | 1/2008 | Chang et al. |
| 7,322,982 B2 | 1/2008 | Vincent-Prestigiacomo |
| 7,335,202 B2 | 2/2008 | Matthis et al. |
| 7,445,627 B2 | 11/2008 | Hawkes et al. |
| 7,585,299 B2 | 9/2009 | Rezach |
| 7,585,314 B2 | 9/2009 | Taylor et al. |
| 7,585,315 B2 | 9/2009 | Donath |
| 7,678,112 B2 | 3/2010 | Rezach |
| 7,678,139 B2 | 3/2010 | Garamszegi et al. |
| 7,686,835 B2 | 3/2010 | Warnick |
| 7,766,915 B2 | 8/2010 | Jackson |
| 7,776,067 B2 | 8/2010 | Jackson |
| 7,819,899 B2 | 10/2010 | Lancial |
| 7,828,829 B2 | 11/2010 | Ensign |
| 7,833,248 B2 | 11/2010 | Markworth et al. |
| 7,862,594 B2 | 1/2011 | Abdelgany |
| 7,892,259 B2 | 2/2011 | Biedermann et al. |
| 2002/0035366 A1 | 3/2002 | Walder et al. |
| 2003/0028192 A1 | 2/2003 | Schar et al. |
| 2003/0125742 A1 | 7/2003 | Yuan et al. |
| 2004/0138660 A1 | 7/2004 | Serhan |
| 2005/0027292 A1 | 2/2005 | Bernard et al. |
| 2005/0080419 A1 | 4/2005 | Donath |
| 2005/0085812 A1 | 4/2005 | Sherman et al. |
| 2005/0096659 A1 | 5/2005 | Freudiger |
| 2005/0154391 A1 | 7/2005 | Doherty et al. |
| 2005/0177156 A1 | 8/2005 | Timm et al. |
| 2005/0192573 A1 | 9/2005 | Abdelgany et al. |
| 2005/0203515 A1 | 9/2005 | Doherty et al. |
| 2005/0216003 A1 | 9/2005 | Biedermann et al. |
| 2005/0273099 A1 | 12/2005 | Baccelli et al. |
| 2005/0277919 A1 | 12/2005 | Slivka et al. |
| 2005/0277923 A1 | 12/2005 | Sweeney |
| 2005/0277924 A1 | 12/2005 | Roychowdhury |
| 2005/0277927 A1 | 12/2005 | Guenther et al. |
| 2005/0277928 A1 | 12/2005 | Boschert |
| 2005/0283157 A1 | 12/2005 | Coates et al. |
| 2006/0025767 A1 | 2/2006 | Khalili |
| 2006/0025768 A1 | 2/2006 | Iott et al. |
| 2006/0036244 A1 | 2/2006 | Spitler et al. |
| 2006/0079894 A1 | 4/2006 | Colleran et al. |
| 2006/0089644 A1 | 4/2006 | Felix |
| 2006/0149244 A1 | 7/2006 | Amrein et al. |
| 2006/0155278 A1 | 7/2006 | Warnick |
| 2006/0173454 A1 | 8/2006 | Spitler et al. |
| 2006/0200128 A1 | 9/2006 | Mueller |
| 2006/0200149 A1 | 9/2006 | Hoy et al. |
| 2006/0229615 A1 | 10/2006 | Abdou |
| 2006/0235393 A1 | 10/2006 | Bono et al. |
| 2007/0043355 A1 | 2/2007 | Bette et al. |
| 2007/0043357 A1 | 2/2007 | Kirschman |
| 2007/0055235 A1 | 3/2007 | Janowski et al. |
| 2007/0055242 A1 | 3/2007 | Bailly |
| 2007/0093817 A1 | 4/2007 | Barrus et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0123860 A1 | 5/2007 | Francis et al. |
| 2007/0123862 A1 | 5/2007 | Warnick |
| 2007/0123865 A1 | 5/2007 | Schlapfer et al. |
| 2007/0123867 A1 | 5/2007 | Kirschman |
| 2007/0162008 A1 | 7/2007 | Cline et al. |
| 2007/0225707 A1 | 9/2007 | Wisnewski et al. |
| 2007/0225708 A1 | 9/2007 | Biedermann et al. |
| 2007/0225711 A1 | 9/2007 | Ensign |
| 2007/0233080 A1 | 10/2007 | Na et al. |
| 2007/0233087 A1 | 10/2007 | Schlapfer |
| 2007/0260246 A1 | 11/2007 | Biedermann |
| 2008/0004627 A1 | 1/2008 | Dalton |
| 2008/0015579 A1 | 1/2008 | Whipple |
| 2008/0027432 A1 | 1/2008 | Strauss et al. |
| 2008/0045956 A1 | 2/2008 | Songer et al. |
| 2008/0058809 A1 | 3/2008 | Graf |
| 2008/0058812 A1 | 3/2008 | Zehnder |
| 2008/0071277 A1 | 3/2008 | Warnick |
| 2008/0154308 A1 | 6/2008 | Sherman et al. |
| 2008/0161859 A1 | 7/2008 | Nilsson |
| 2008/0161863 A1 | 7/2008 | Arnold et al. |
| 2008/0183214 A1 | 7/2008 | Copp et al. |
| 2008/0183216 A1 | 7/2008 | Jackson |
| 2008/0195156 A1 | 8/2008 | Ainsworth et al. |
| 2008/0234734 A1 | 9/2008 | Walder et al. |
| 2008/0234757 A1 | 9/2008 | Jacofsky et al. |
| 2008/0249570 A1 | 10/2008 | Carson et al. |
| 2009/0005817 A1 | 1/2009 | Friedrich et al. |
| 2009/0012567 A1 | 1/2009 | Biedermann et al. |
| 2009/0069849 A1 | 3/2009 | Oh et al. |
| 2009/0118767 A1 | 5/2009 | Hestad et al. |
| 2010/0010544 A1 | 1/2010 | Fallin et al. |
| 2010/0094344 A1 | 4/2010 | Trieu |
| 2010/0094349 A1 | 4/2010 | Hammer et al. |
| 2010/0114168 A1 | 5/2010 | Miller |
| 2010/0114170 A1 | 5/2010 | Barrus et al. |
| 2010/0174313 A1 | 7/2010 | Abdelgany et al. |
| 2010/0234891 A1 | 9/2010 | Freeman et al. |
| 2010/0249845 A1 | 9/2010 | Meunier et al. |
| 2010/0298884 A1 | 11/2010 | Faizan et al. |
| 2010/0312279 A1 | 12/2010 | Gephart et al. |
| 2010/0312282 A1 | 12/2010 | Abdou |
| 2010/0331886 A1 | 12/2010 | Fanger et al. |
| 2010/0331887 A1 | 12/2010 | Jackson et al. |
| 2011/0004245 A1 | 1/2011 | Wu et al. |
| 2011/0077689 A1 | 3/2011 | Mickiewicz et al. |

OTHER PUBLICATIONS

Office Action issued in U.S. Appl. No. 12/174,484, mailed Apr. 15, 2011, 14 pages.

Office Action issued in U.S. Appl. No. 12/165,724, mailed Jul. 25, 2011, 7 pages.

* cited by examiner

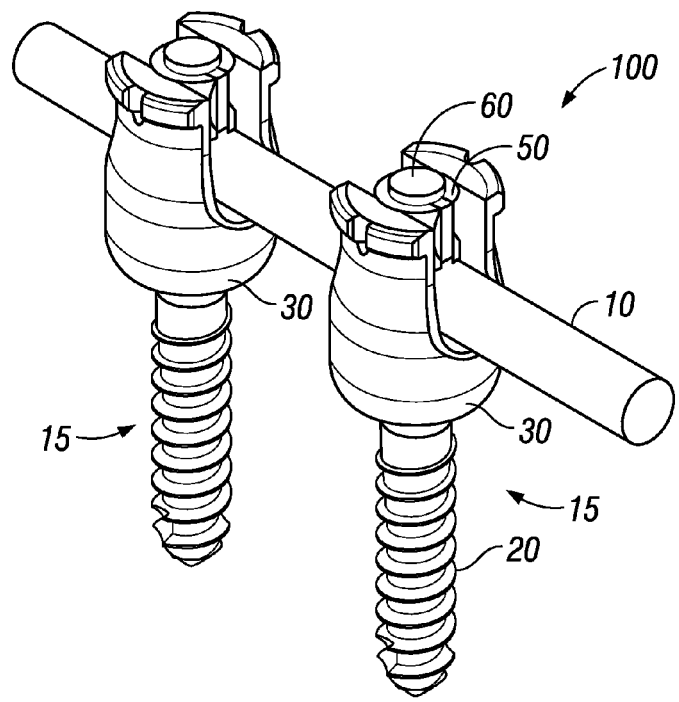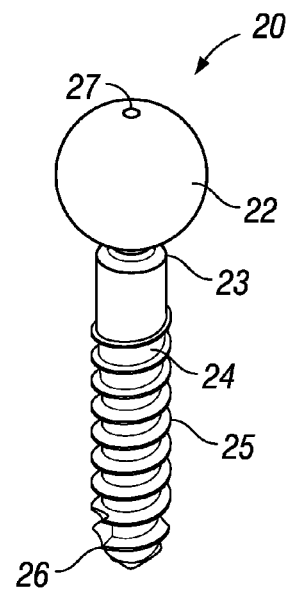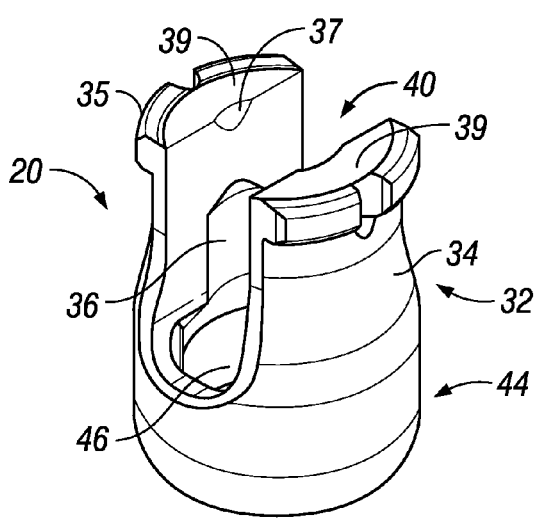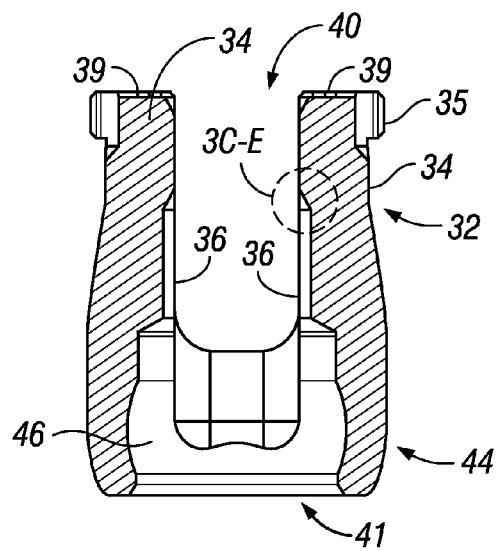
FIG. 1
FIG. 2
FIG. 3A
FIG. 3B

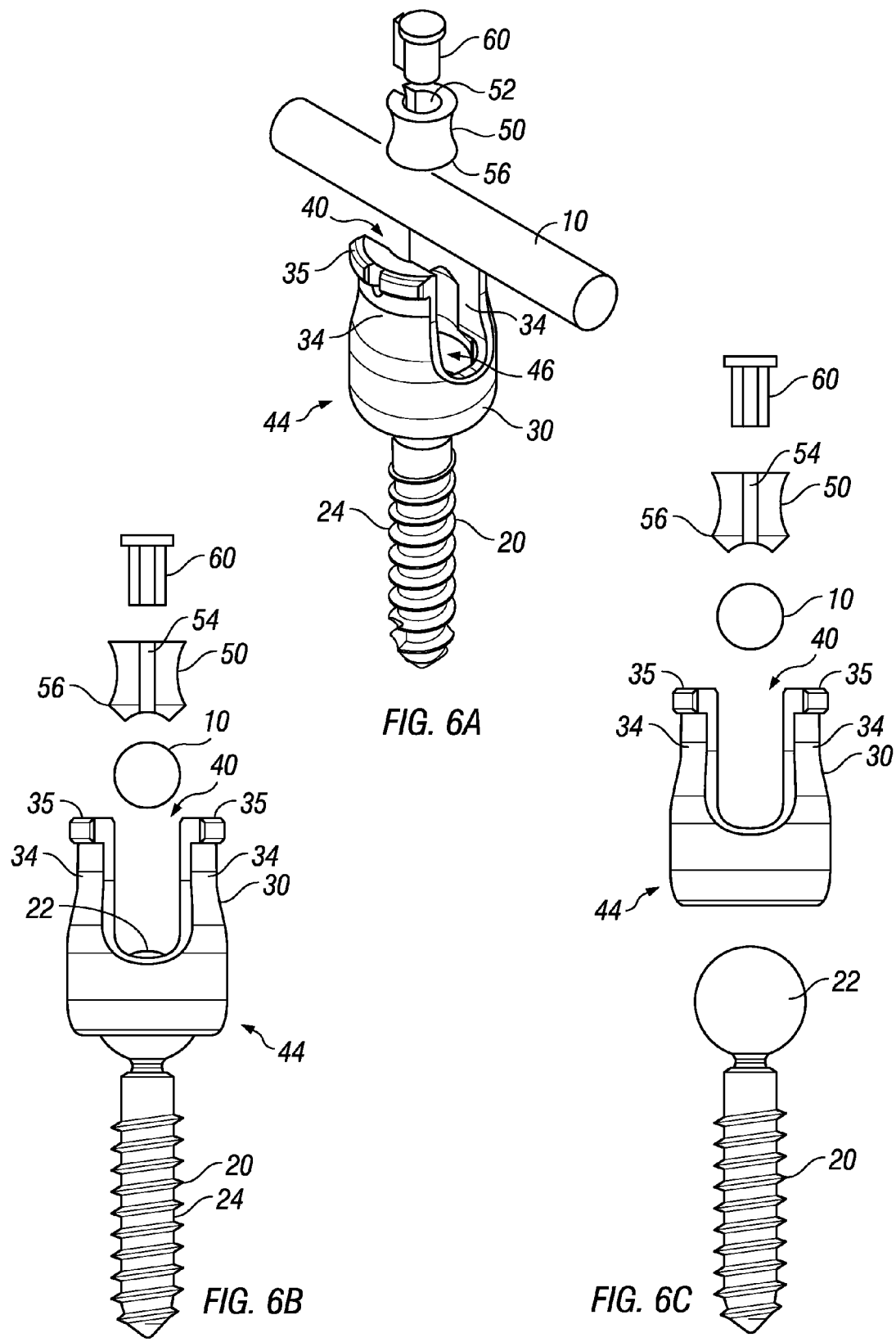

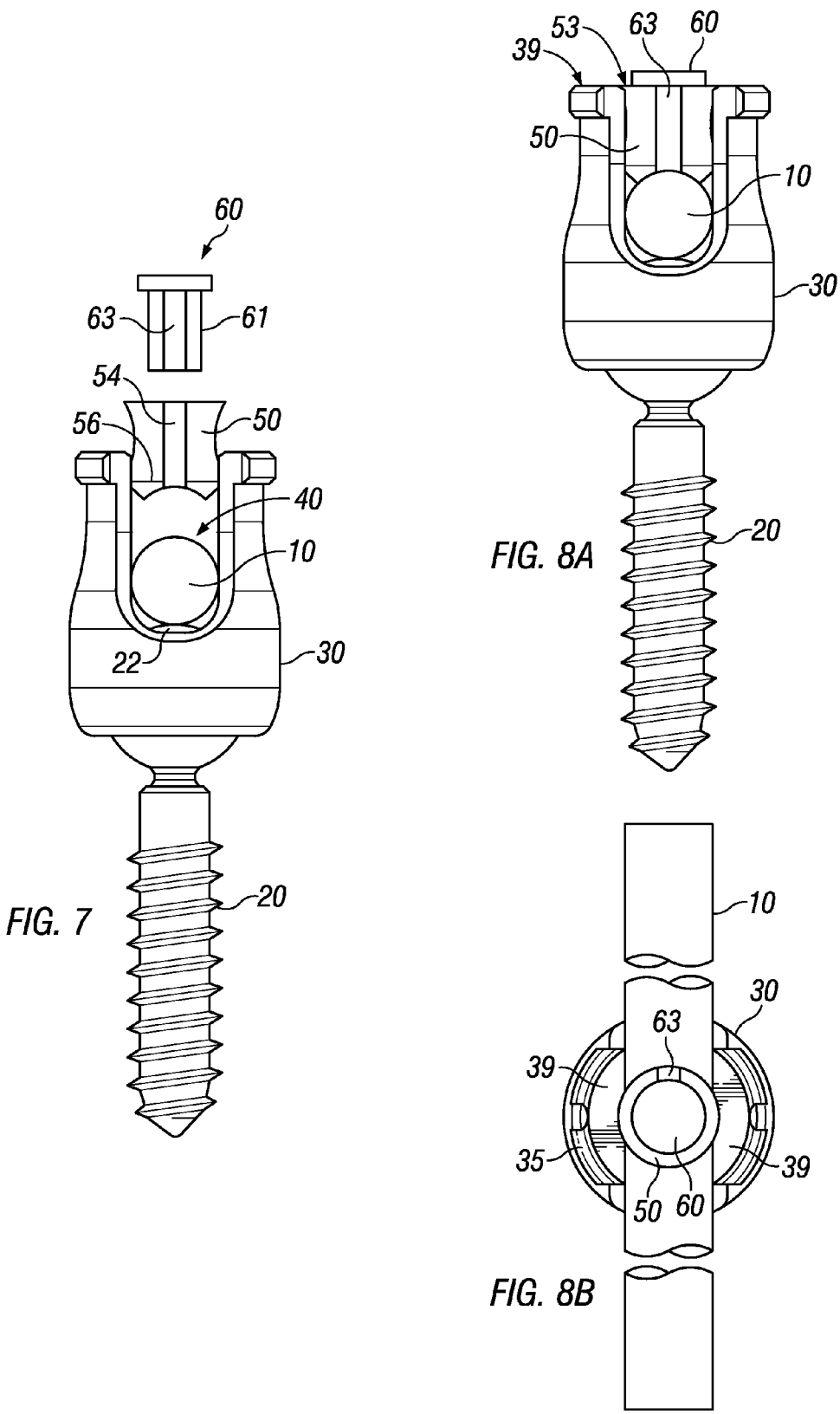

LOCKING INSERT FOR SPINE STABILIZATION AND METHOD OF USE

BACKGROUND

1. Field of the Disclosure

The present disclosure generally relates to spinal stabilization systems. Embodiments of the disclosure relate to spinal stabilization systems that may have non-threaded portions for securing rods to bone fasteners.

2. Description of Related Art

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Spinal stabilization systems for a lumbar region of the spine may be inserted during a spinal stabilization procedure using a posterior spinal approach. Minimally invasive procedures and systems may reduce recovery time as well as trauma to the soft tissue surrounding a stabilization site.

SUMMARY

A spinal stabilization system may be installed in a patient to stabilize a portion of a spine. A spinal stabilization system may be installed using a minimally invasive procedure. An instrumentation kit may provide instruments and spinal stabilization system components necessary for forming a spinal stabilization system in a patient.

A spinal stabilization system may be used to achieve rigid pedicle fixation while minimizing the amount of damage to surrounding tissue. In some embodiments, a spinal stabilization system may be used to provide stability to two or more vertebrae. A spinal stabilization system may include a rod, two or more bone fastener assemblies, and/or a resilient insert. The bone fastener assembly may include, but is not limited to, a bone fastener and a collar. A first portion of the bone fastener may couple to a portion of the spine during use. A first portion of a collar may couple to a second portion of the bone fastener. A second portion of the collar may couple to a rod during use. In some embodiments, an orientation of the bone fastener may be independent of the orientation of the collar for a bone fastener assembly. After the bone fastener is placed in a vertebral body, the collar coupled to the bone fastener may be positioned so that the rod can be positioned in the collar and in at least one other collar that is coupled to another vertebral body by a bone fastener.

Embodiments disclosed herein are directed to an apparatus for securing a rod to a bone fastener. In some embodiments, the apparatus may include a collar, a resilient insert, and a pin. In some embodiments, a first end comprises two arms and a channel defined by the two arms. The channel may have a geometric configuration that accommodates a rod. In some embodiments, the second end comprises an opening opposite the first end and recessing at least partially into the second end of the collar to form a cavity. In some embodiments, the apparatus may include a resilient insert having a central passage centered about the longitudinal axis of the resilient insert and running the length of the resilient insert and a slot connected to the central passage and running the length of the resilient insert. In some embodiments, the resilient insert has an outer diameter greater than the width of the channel when the resilient insert is in a neutral state. In some embodiments, radial compression of the resilient insert decreases the outer diameter of the resilient insert such that the resilient insert is insertable into the channel. Insertion of the resilient insert into the recessed portions of the two arms allows the outer diameter of the resilient insert to increase to inhibit passage of the resilient insert out of the recessed portions. In some embodiments, the apparatus may include a pin having a central core for insertion into the central passage of the resilient insert and a radial extension having a selected thickness for insertion into the slot of the resilient insert. In some embodiments, insertion of the pin into the resilient insert inhibits the outer diameter of the resilient insert from decreasing. In some embodiments, a portion of the radial extension of the pin has a selected thickness greater than the width of the slot. In some embodiments, the radial extension on the pin has a tapered thickness, wherein insertion of the pin into the resilient insert increases the outer diameter of the resilient insert to a diameter greater than the outer diameter of the resilient insert in a neutral state. In some embodiments, advancement of the pin into the resilient insert creates a cold weld between the pin, the resilient insert and the two arms. In some embodiments, the recessed portions have an associated radius of curvature or angle. In some embodiments, positioning the resilient insert in the recessed portions of the two arms exerts a downward force on the resilient insert for increased friction contact with a rod. In some embodiments, a head of a bone fastener is positionable into the cavity, wherein advancement of the pin into the resilient insert creates a cold weld between the resilient insert, a rod positioned in the channel, and the head of a bone fastener positioned in the cavity.

Embodiments disclosed herein are directed to a system for coupling a rod to a vertebra. The system may include a rod having a substantially circular cross-sectional geometry, two or more bone fasteners, two or more anchor assemblies, a resilient insert and a pin. Each bone fastener may comprise a threaded shank and a head connected to the threaded shank. Each anchor assembly may have a collar with a first end and a second end. The first end may include two arms, wherein each arm comprises a recessed portion on an inner surface, and a channel defined by the two arms, wherein the rod is positionable in the channel. The second end may include an opening opposite the first end and recessing at least partially into the second end of the collar to form a cavity. The resilient insert may have a central passage centered about the longitudinal axis of the resilient insert and running the length of the resilient insert and a slot connected to the central passage and running the length of the resilient insert. In some embodiments, the resilient insert has an outer diameter greater than the width of the channel when the resilient insert is in a neutral state. In some embodiments, radial compression of the resilient insert decreases the outer diameter of the resilient insert such that the resilient insert is insertable into the channel. In some embodiments, insertion of the resilient insert into the recessed portions of the two arms allows the outer diameter of the resilient insert to increase to inhibit passage of the resilient insert out of the recessed portions. The pin may have a central core for insertion into the central passage of the resilient insert and a radial extension with a selected thickness for insertion into the slot of the resilient insert. In some embodiments, insertion of the pin into the resilient insert inhibits the outer diameter of the resilient insert from decreasing, wherein the resilient insert maintains the rod and the head of the bone fastener in the anchor assembly. In some embodiments, a portion of the radial extension of the pin has a selected thickness greater than the width of the slot. In some embodiments, the radial extension of the pin has a tapered thickness, wherein insertion of the pin into the resilient insert increases the outer diameter of the resilient insert to a diameter greater than the outer diameter of the resilient insert in a neutral state. In some embodiments, advancement of the pin into the resilient insert creates a cold weld between the pin, the resilient insert and the two arms. In some embodiments, the recessed portions have a radius of curvature. In some embodiments, positioning the resilient insert in the recessed portions of the two arms exerts a downward force on the resilient insert for increased friction contact with a rod. In some embodiments, advancement of the pin into the resilient insert creates a cold weld between the resilient insert, a rod positioned in the channel, and the head of a bone fastener positioned in the cavity.

Embodiments disclosed herein are directed to a method for coupling a rod to a vertebra. The method may include the steps of advancing a bone fastener into a vertebral body, coupling an anchor assembly to the head of the bone fastener, positioning a portion of a rod into a channel in the anchor assembly, radially compressing a resilient insert, inserting a resilient insert into the channel, inserting the resilient insert into the recessed portions of the arms, and inserting a pin into the resilient insert to maintain the outer diameter of the resilient insert greater than the width of the channel to inhibit passage of the resilient insert out of the recessed portions. Bone fasteners may comprise a head having a curved surface and a threaded shank connected to the head. Anchor assemblies may have a collar with a first end and a second end. The first end may include two arms, wherein each arm has a recessed portion on an inner surface, and a channel defined by the two arms, wherein the rod is positionable in the channel. The second end may have an opening opposite the first end and recessing at least partially into the second end of the collar to form a cavity. The resilient insert may have a central passage centered about the longitudinal axis of the resilient insert and running the length of the resilient insert. The resilient insert may have a slot connected to the central passage and running the length of the resilient insert. In some embodiments, the resilient insert has an outer diameter greater than the width of the channel when the resilient insert is in a neutral state. In some embodiments, the outer diameter is less than the width of the channel when the resilient insert is radially compressed. In some embodiments, the outer diameter of the resilient insert is greater than the width of the channel when the resilient insert is positioned in the recessed portions of the arms. In some embodiments, the pin has a central core for insertion into the central passage of the resilient insert and a radial extension with a selected thickness for insertion into the slot of the resilient insert. In some embodiments, the method further includes making an incision in a patient and advancing one or more of the anchor assembly and the rod through the incision using Minimally Invasive Surgery (MIS) procedures. In some embodiments, a portion of the radial extension of the pin is equal to the width of the slot, wherein the radius of curvature is equal to the width of the channel. In some embodiments, the thickness of the radial extension of the pin is greater than the width of the slot. In some embodiments, the radial extension on the pin has a tapered thickness, wherein inserting the pin into the resilient insert increases the outer diameter of the resilient insert to a diameter greater than the outer diameter of the resilient insert in a neutral state. In some embodiments, inserting the pin into the resilient insert creates a cold weld between the pin, the resilient insert and the two upwardly extending arms. In some embodiments, the recessed portions have a radius of curvature. In some embodiments, positioning the resilient insert in the recessed portions of the two upwardly extending arms exerts a downward force on the resilient insert for increased friction contact with a rod. In some embodiments, inserting the pin into the resilient insert creates a cold weld between the lower surface of the resilient insert, the rod positioned in the channel, and the head of a bone fastener positioned in the cavity.

Different instruments may be used in a Minimally Invasive Surgery (MIS) procedure to form a spinal stabilization system in a patient. The instruments may include, but are not limited to, positioning needles, guide wires, sleeves, bone fastener driver, mallets, tissue wedges, tissue retractors, tissue dilators, bone awls, taps, and a rod length estimator. An instrumentation kit may include, but is not limited to, two or more detachable members (e.g., sleeves), a tissue wedge, a rod positioner, an estimating tool, a seater, insert driver, and/or combinations thereof.

BRIEF DESCRIPTION OF THE DRAWINGS

Advantages of the present disclosure will become apparent to those skilled in the art with the benefit of the following detailed description and upon reference to the accompanying drawings in which:

FIG. 1 depicts a perspective view of one embodiment of a spinal stabilization system;

FIG. 2 depicts a perspective view of one embodiment of a bone fastener;

FIGS. 3A and 3B depict perspective and side views of one embodiment of a collar;

FIGS. 6A-6C depict perspective and side exploded views of one embodiment of a portion of a spine stabilization system;

FIG. 7 depicts a side view of one embodiment of a portion of a spine stabilization system; and FIGS. 8A and 8B depict side and top views of one embodiment of a portion of a spine stabilization system.

Figure 3C:
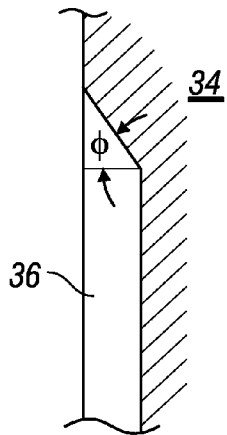
FIGS. 3C-3E depict section views of embodiments of recessed portion in the collar depicted in FIGS. 3A and 3B.

While the disclosure is susceptible to various modifications and alternative forms, specific embodiments thereof are shown by way of example in the drawings and will herein be described in detail. The drawings may not be to scale. It should be understood that the drawings and detailed description thereto are not intended to limit the disclosure to the particular form disclosed, but on the contrary, the intention is to cover all modifications, equivalents, and alternatives falling within the spirit and scope of the present disclosure as defined by the appended claims.

DETAILED DESCRIPTION

The disclosure and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach.

A spinal stabilization system may be used to achieve rigid fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. A rod may be coupled and secured to the bone fastener assemblies. As used herein, "coupled" components may directly contact each other or may be separated by one or more intervening members. In some embodiments, a single spinal stabilization system may be installed in a patient. Such a system may be referred to as a unilateral, single-level stabilization system or a single-level, two-point stabilization system. In some embodiments, two spinal stabilization systems may be installed in a patient on opposite sides of a spine. Such a system may be referred to as a bilateral, single-level stabilization system or a single-level, four-point stabilization system.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. A rod may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system.

In some embodiments, combination systems may be installed. For example, a two-point stabilization system may be installed on one side of a spine, and a three-point stabilization system may be installed on the opposite side of the spine. The composite system may be referred to a five-point stabilization system.

Minimally invasive procedures may reduce trauma to soft tissue surrounding vertebrae that are to be stabilized. Only a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized. In some embodiments, the incision may be above and between the vertebrae to be stabilized. In some embodiments, the incision may be above and substantially halfway between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures. A minimally invasive procedure may reduce recovery time for the patient as compared to invasive spinal procedures.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

FIG. 1 depicts one embodiment of spinal stabilization system 100 that may be implanted through a minimally invasive surgical procedure. Spinal stabilization system 100 may include rod 10 and bone fastener assemblies 15 including bone fasteners 20, collars 30, resilient inserts 50 and pins 60. Other spinal stabilization system embodiments may include, but are not limited to, plates, dumbbell-shaped members, and/or transverse connectors. FIG. 1 depicts a spinal stabilization system for one vertebral level. In some embodiments, the spinal stabilization system of FIG. 1 may be used as a multi-level spinal stabilization system if one or more vertebrae are located between the vertebrae in which bone fastener assemblies 15 are placed. In some embodiments, multi-level spinal stabilization systems may include additional bone fastener assemblies 15 to couple to one or more other vertebrae.

FIG. 2 depicts a perspective view of one embodiment of bone fastener 20. In some embodiments, bone fastener 20 may include shank 24 and head 22. In some embodiments, bone fastener 20 may include shank 24, neck 23 and head 22. Shank 24 may include threading 25. In some embodiments, threading 25 may include self-tapping start 26. Self-tapping start 26 may facilitate insertion of bone fastener 20 into vertebral bone. Bone fasteners 20 may be provided in various lengths in an instrumentation set to accommodate variability in vertebral bodies. For example, an instrumentation set for stabilizing vertebrae in a lumbar region of the spine may include bone fasteners 20 with lengths ranging from about 30 mm to about 75 mm in 5 mm increments. A bone fastener 20 may be stamped with indicia (i.e., printing on the head). In some embodiments, bone fastener 20 may be color-coded to indicate a length of bone fastener 20. In some embodiments, bone fastener 20 with a 30 mm thread length may have a magenta color, a bone fastener with a 35 mm thread length may have an orange color, and a bone fastener with a 55 mm thread length may have a blue color. Other colors may be used as desired.

Each bone fastener 20 provided in an instrumentation set may have substantially the same thread profile and thread pitch. In one embodiment, the thread may have about a 4 mm major diameter and about a 2.5 mm minor diameter with a cancellous thread profile. In some embodiments, the minor diameter of the thread may be in a range from about 1.5 mm to about 4 mm or larger. In some embodiments, the major diameter of the thread may be in a range from about 3.5 mm to about 6.5 mm or larger. Bone fasteners 20 with other thread dimensions and/or thread profiles may also be used. A thread profile of bone fasteners 20 may allow bone purchase to be maximized when bone fastener 20 is positioned in vertebral bone.

In some embodiments, head 22 of bone fastener 20 may include various configurations or geometries to couple with a resilient insert 50. In some embodiments, spherical head 22 may provide some polyaxial movement of collar 30 relative to bone fastener 20. In some embodiments, head 22 may have a substantially circular cross-sectional geometry as shown in FIG. 2. In some embodiments, head 22 may be shaped with a spherical geometry. In some embodiments, head 22 may have a substantially spherical geometry. The surface of head 22 of bone fastener 20 may be machined for selected contact with resilient insert 50. Head 22 may be grooved, knurled, bead blasted, or otherwise machined for increased friction contact between head 22 and resilient insert 50. In some embodiments, head 22 may include various configurations for engagement by a driver or other tool. In some embodiments, a driver may also be used to remove an installed bone fastener 20 from a vertebra. In some embodiments, bone fastener 20 may be cannulated for use in a minimally invasive procedure. In some embodiments, cannulated passage 27 may run along longitudinal axis CY of bone fastener 20.

In some embodiments, head 22 or shank 24 may limit the angulation or rotation of collar 30 about bone fastener 20. In some embodiments, bone fastener 20 may include neck 23. In some embodiments, neck 23 of bone fastener 20 may have a smaller diameter than adjacent portions of head 22 and shank 24. The diameter of neck 23 may fix the maximum angle that collar 30 can rotate relative to bone fastener 20. In some embodiments, neck 23 may be sized to allow up to about 40 degrees or more of angulation of collar 30 relative to bone fastener 20. In some embodiments, neck 23 may be sized to allow up to about 30 degrees or more of angulation of collar 30 relative to bone fastener 20. In some embodiments, neck 23 may be sized to allow up to about 20 degrees or more of angulation of collar 30 relative to bone fastener 20.

FIGS. 3A and 3B depict perspective and side views of one embodiment of collar 30. In some embodiments, collar 30 may be used to couple rod 10 to bone fastener 20 engaged in a vertebral body. Multiple collars 30 coupling rod 10 to multiple vertebrae may stabilize a portion of the spine. Collar 30 may receive elements including, but not limited to, bone fastener 20, resilient insert 50, pin 60 and rod 10. In some embodiments, collar 30 may couple two or more elements together. Collar 30 may have any of various physical forms. In some embodiments, rod 10 may be seated in collar 30. Resilient insert 50 may be inserted in collar 30 to secure rod 10 in collar 30.

Collar 30 may include first end 32 having channel 40 defined by arms 34. First end 32 may include channel 40. Collar 30 may include second end 44 having opening 41 recessing into second end 44 to form cavity 46.

In some embodiments, channel 40 may be formed to have a geometric configuration having a constant width, a variable width, an angular opening, a curved opening, a tapered opening, and combinations and/or portions thereof. The geometric configuration of channel 40 may accommodate rod 10. In some embodiments, the width of channel 40 may be substantially the same as the diameter of rod 10 having a circular cross-sectional geometry. In some embodiments, the width of channel 40 may be such that arms 34 may resist movement of rod 10 in collar 30. In some embodiments, the width of channel 40 may be such that arms 34 provide little resistance to movement of rod 10 in collar 30. The depth of channel 40 may accommodate rod 10, resilient insert 50 and pin 60. In some embodiments, channel 40 may be deep enough such that rod 10, resilient insert 50 and pin 60 are below top surface 39 of collar 30. The base of channel 40 may be curved, angled, or some combination thereof to accommodate rod 10.

In some embodiments, arms 34 may include flanges 35 for engagement with various tools. Flanges 35 may be useful for engagement by a tool. Embodiments disclosed herein may not require torque to insert resilient inserts 50 or pins 60. During implantation, collar 30 may be exposed to only compressive, tensile, or shear forces. Flange 35 may provide sufficient support for the tensile, compressive and shear forces used to position resilient insert 50. If the surgeon needs to remove or withdraw resilient insert 50 from collar 30, flange 35 may be engaged by the tool. The tool may engage flanges 35. By pushing down on collar 30 or flange 35 and pulling up on resilient insert 50, resilient insert 50 may be removed without allying torques to resilient insert 50 or collar 30.

In some embodiments, indentations 37 may be useful for guiding resilient insert 50 into recessed portions 36. In some embodiments, arms 34 may include indentations 37. Indentations 37 may be helpful radially compressing resilient insert 50 during insertion. For example, resilient insert 50 may be inserted into collar 30 by pushing resilient insert 50 into indentations 37 while pulling on collar 30. As resilient insert 50 advances in indentations 37 and arms 36, resilient insert 50 may compress radially. Continued pushing on resilient insert 50 and simultaneous pulling on flange 35 of collar 30 may advance resilient inert 50 into recessed portions 36. In some embodiments, indentations 37 may not be continuous from the edge of arm 34 to recessed portions 36. In some embodiments, indentations 37 may be only on the edge of arms 34. In some embodiments, having indentations 37 formed in a portion of arm 34 may enable a surgeon to pre-position resilient insert 50. Pre-positioning resilient insert 50 may facilitate insertion of resilient insert 50 in arms 34.

In some embodiments, collar 30 may include second end 44 having opening 41 opposite first end 32. In some embodiments, opening 41 recesses into second end 44 to form cavity 46. In some embodiments, cavity 46 may recess into first end 32 to connect with channel 40, which may allow shank 24 of bone fastener 20 to be advanced into channel 40 such that shank 24 passes through collar 30 and head 22 is advanced into cavity 41. Cavity 46 may be spherical or otherwise curved to accommodate head 22 of bone fastener 108. Cavity 46 may have a diameter that is larger than the width of channel 40. In some embodiments, arms 34 may be deflected outward to allow head 22 of bone fastener 20 to pass through first end 32. In some embodiments, bone fastener assembly 15 may be partially pre-assembled such that head 22 of bone fastener 20 is positioned in cavity 46. Pre-assembled bone fastener assemblies 15 may reduce the likelihood of collar 30 disengaging from bone fastener 20. Pre-assembled bone fastener assemblies 15 may still allow bone fastener 20 to rotate in collar 30 for ease of implantation, positioning, adjustment, or the like. Second end 44 of collar 30 may be larger or smaller than first end 32. Having first end 32 smaller than second end 44 may be advantageous for spine stabilization. During surgery, visualization of components may be necessary. Smaller portions of collar 30 may provide more visualization of other elements, the implantation site, etc.

In some embodiments, each arm 34 may have recessed portion 36. Recessed portions 36 may be machined in arms 34 to accommodate resilient insert 50. Recessed portions 36 may be machined to complement a portion of an outer surface of resilient insert 50 that is to be positioned in collar 30. Machining of recessed portions 36 may enhance retention of resilient insert 50 in collar 30. Recessed portions 36 may be complementary in shape to a portion of resilient insert 50 so that resilient insert 50 is inhibited from withdrawing from collar 30. Recessed portions 36 may have a concave or angled profile.

The shape, depth, profile, length, surface texture, and other characteristics of recessed portions 36 may be selected to provide a desired force or resistance force on resilient insert 50 and/or rod 10. In some embodiments, the increase in downward force may be linear due to the linear change in the depth of recessed portions 36. In some embodiments, the increase in downward force may be based on the spring constant associated with radially compressing resilient insert 50. In some embodiments, the increase in downward force may be based on the combination of the depth of recessed portions 36 and the spring constant of resilient insert 50.

FIG. 3C depicts a cross-section detail view of one embodiment of recessed portions 36 in the embodiment of collar 30 depicted in FIGS. 3A and 3B. In some embodiments, such as depicted in FIG. 3C, recessed portions 36 may have a linear change in depth with an associated angle $\Phi$(phi). Collar 30 with arms 34 having recessed portions 36 with a linear change in depth may exert a downward force on rod 10. In some embodiments, recessed portions 36 may provide little downward force. In some embodiments, recessed portions 36 may be only slightly recessed, such that the downward force is almost negligible. In some embodiments, recessed portions 36 may have a portion oriented nearly perpendicular to arms 34, such that little downward force is exerted on resilient insert 50 even though resilient insert 50 may be inhibited from withdrawing from recessed portions 36. In some embodiments, the downward force may increase proportionately. In some embodiments, the downward force exerted by resilient insert 50 on rod 10 may increase linearly. In some embodiments, the downward force exerted by resilient insert 50 on rod 10 may increase proportionately to the spring constant of resilient insert 50 (discussed below).

In some embodiments, in order for resilient insert 50 to be withdrawn from recessed portions 36, resilient insert 50 must compress radially (i.e., the outer diameter of resilient insert 50 must be less than the width of channel 40). In some embodiments, the force required to compress resilient insert 50 is less than the force required to withdraw resilient insert 50 from arms 34 (i.e., the force exerted to withdraw resilient insert 50 from arms 34 must be high enough to radially compress resilient insert 50 such that the radius of curvature of resilient insert 50 is less than the width of channel 40). In some embodiments, if recessed portions 36 have an angle $\phi$ (phi) of substantially 0 degrees (i.e. recessed portions 36 are almost non-existent), recessed portions 36 may require little radial compression for resilient insert 50 to be withdrawn from arms 34 (i.e., the force exerted on resilient insert 50 by recessed portions 36 during withdrawal of resilient insert 50 may be approximately 0 lbs). If recessed portions 36 have an angle $\Phi$ (phi) of substantially 90 degrees (i.e., recessed portions 36 extend almost perpendicular to channel 40), recessed portions 36 may require high radial compression for resilient insert 50 to be withdrawn from recessed portions 36 (i.e., resilient insert 50 must be compressed radially before resilient insert 50 can be withdrawn). If recessed portions 36 have an angle $\phi$ (phi) of approximately 45 degrees, resilient insert 50 may require some radial compression (i.e., the radius of curvature of resilient insert 50 may decrease as resilient insert 50 is withdrawn from recessed portions 36.

Figure 3D:
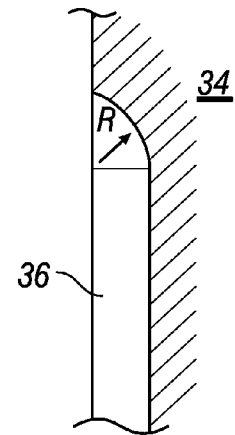

FIG. 3D depicts a cross-section detail view of one embodiment of collar 30 of FIGS. 3A and 3B. In FIG. 3D, recessed portions 36 have a curved profile, with an associated radius of curvature R. Collar 30 with arms 34 having recessed portions 36 of a selected radius of curvature R may exert a downward force on rod 10 based on the position of resilient insert 50 in recessed portions 36. In some embodiments, the downward force may change non-linearly. In some embodiments, the downward force may increase at a greater rate than the change in the position of resilient insert 50 in recessed portions 36. In some embodiments, if the radius of curvature R of recessed portions 36 is large (i.e., recessed portions 36 are almost non-existent), recessed portions 36 may provide a substantially negligible downward force. If recessed portions 36 have radius of curvature R that is small (i.e., recessed portions 36 have a very sharp curve), recessed portions 36 may provide higher downward forces.

In some embodiments, the force required to withdraw resilient insert 50 from arms 34 may be less than a force needed to radially compress resilient insert 50. In some embodiments, if the radius of curvature R of recessed portions 36 is large, recessed portions 36 may provide little resistance to removal of resilient insert. If recessed portions 36 have radius of curvature R that is small (i.e., recessed portions 36 have a very sharp curve), recessed portions 36 may provide higher resistance to removal of resilient insert 50 from arms 34. In some embodiments, withdrawal of resilient insert 50 from recessed portions 36 may involve radially compressing resilient insert 50 before attempting to withdraw resilient insert 50 from recessed portions 36. In some embodiments, if the radius of curvature R of recessed portions 36 is small, resilient insert 50 may need to be compressed radially before attempting to remove resilient insert 50 from recessed portions 36.

Figure 3E:
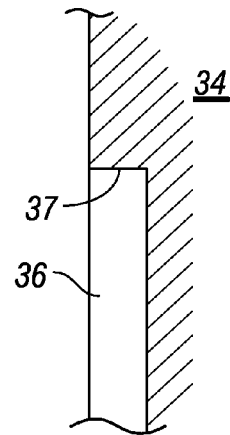

FIG. 3E depicts a cross-section detail view of a one embodiment of collar 30 having recessed portions 36 in arms 34. In some embodiments, recessed portions 36 may have angled sides 37 for abutting resilient insert 50. In some embodiments, recessed portions 36 having angled sides 37 may resist withdrawal of resilient insert 50 from arms 34. In some embodiments, if the depth of recessed portions 36 is small (i.e., the length of side 37 is approximately 0) the force required to insert or withdraw resilient insert 50 may be small. If the length of side 37 is large, resilient insert 50 may need to be radially compressed before insertion into arms 34 or withdrawal from arms 36.

In some embodiments, resilient insert 50 may be advanced into recessed portions 36 (such as depicted in FIGS. 3C-3E) in collar 30 to retain rod 10 in collar 30. FIGS. 4A-4D depict perspective, side, bottom and top views of one embodiment of resilient insert 50.

FIGS. 4A-4D depict resilient insert 50 prior to insertion of resilient insert 50 into collar 30 of bone fastener assembly 15. In some embodiments, resilient insert 50 may include central passage 52 centered about the longitudinal axis of resilient insert 50. Central passage 52 may run the length of resilient insert 50. Central passage 52 may have an associated inner diameter or radius of curvature. In some embodiments, central passage 52 may have a first inner diameter when resilient insert 50 is in a neutral state (i.e., has width $w_1$) and a second inner diameter when resilient insert 50 is compressed (i.e., has width $w_2$). In some embodiments, changing the inner diameter or radius of curvature changes the friction force exerted by resilient insert 50 against arms 34 of collar 30. Changing the friction force can change the rigidity of spine stabilization system 100. Reducing the diameter of resilient insert 50 radially compresses resilient insert 50 to reduce the radius of curvature of central passage 52. In some embodiments, resilient insert 50 may not be inserted into collar 30 unless the radius of curvature of central passage 52 is reduced. In some embodiments, resilient insert 50 may not be withdrawn from collar 30 unless the radius of curvature of central passage 52 is reduced.

In some embodiments, resilient insert 50 may include slot 54 connected to central passage 52 and running the length of resilient insert 50. Slot 54 may define an arclength around central passage 52 or may have a substantially constant width. In some embodiments, slot 54 may be tapered such that the width of slot 54 is wider at one end of resilient insert 50 and thinner at the other end of resilient insert 50. In some embodiments, slot 54 is tapered such that slot 54 is wider at top surface 51 than at bottom surface 53. In some embodiments, slot 54 has a substantially constant width.

Figure 4A:
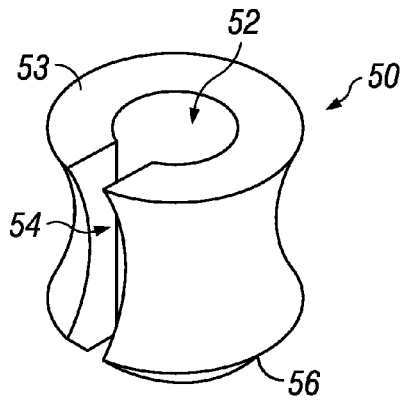
FIGS. 4A-4D depict perspective, bottom and side views of embodiments of a resilient insert.
Figure 4B:
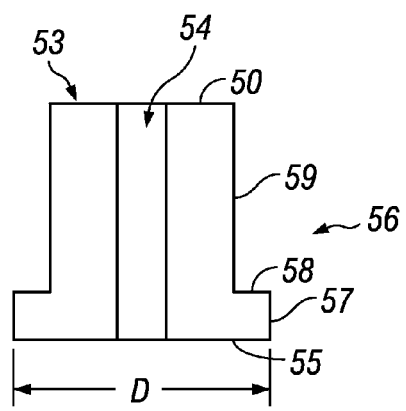
Figure 4C:
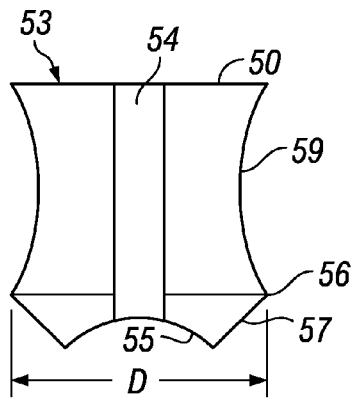

Resilient insert 50 may include ridge 56 for engagement in recessed portions 36. FIGS. 4A-4C depict embodiments of resilient insert 50 having ridge 56. Ridge 56 may be angular or arcuate, and may be arcuate or angular or both. FIG. 4B depicts resilient insert 50 having angular ridge 56 formed by sides 55, 57, 58 and 59. Angular ridge 56 may be used with recessed portion 36 depicted in FIG. 3E to inhibit withdrawal of resilient insert 50 from recessed portions 36. By radially compressing resilient insert 50, the diameter D may be reduced to allow ridge 56 to pass through arms 34. In some embodiments, the diameter D of resilient insert 50 may be greater than the width of channel 40 so that ridge 56 seats in recessed portions 36. By radially compressing resilient insert 50, a portion of the width of slot 54 may be substantially reduced to allow ridge 56 to pass through arms 34.

FIG. 4B depicts a side view of one embodiment of resilient insert 50 having angular sides 55, 57 and 59. In some embodiments, bottom surface 55 may be substantially flat, as depicted in FIG. 4B. In some embodiments, sides 59 that run parallel with central passage 52 may provide higher friction contact with arms 34.

FIG. 4C depicts resilient insert 50 with ridge 56 formed by the junction of two curved or angled surfaces. Ridge 56 having curved or angled surfaces may enable resilient insert 50 to radially compress as ridge 55 contacts arms 34. In some embodiments, during insertion, as surface 57 of resilient insert 50 contacts top surface 39 of collar 30, continued advancement of resilient insert 50 generates a radial force on resilient insert 50. If the radial force exerted on resilient insert exceeds the spring constant of resilient insert 50, resilient insert 50 may compress radially until the diameter D of resilient insert 50 is less than the width of channel 40. Similarly, extracting resilient insert 50 may result in surface 59 contacting arms 34. Continued withdrawal may result in arms 34 radially compressing surface 59 until the diameter D of resilient insert 50 is less than the width of channel 40. One advantage of this type of embodiment may be that a tool for radial compression of resilient insert 50 may not be necessary. Fewer tools may be required, or less complex tools and procedures may be required for inserting resilient insert 50 in collar 30.

Figure 4D:
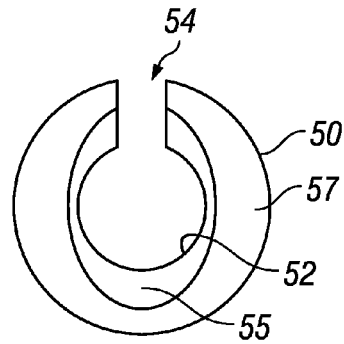

FIG. 4D depicts a bottom view of one embodiment of resilient insert 50. In some embodiments, resilient insert 50 may be machined or contoured for contact with rod 20. In some embodiments, surface 55 may be concave, shaped in the form of a saddle or some other shape for contact with rod 10. In some embodiments, surface 55 having a major axis or minor axis may be aligned with rod 10 such that resilient insert 50 seats in collar 30 when surface 55 aligns a major axis of resilient insert 50 with the longitudinal axis of rod 10. In some embodiments, when resilient insert 50 seats in collar 30, surface 55 in contact with rod 10 may prevent resilient insert 50 from turning.

Figure 5A:
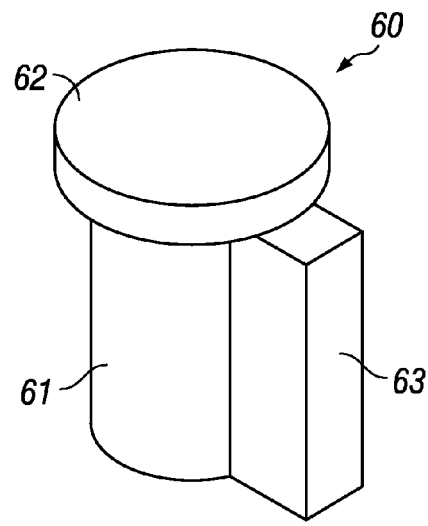
FIGS. 5A-5F depict perspective, bottom and side views of embodiments of a pin.
Figure 5D:
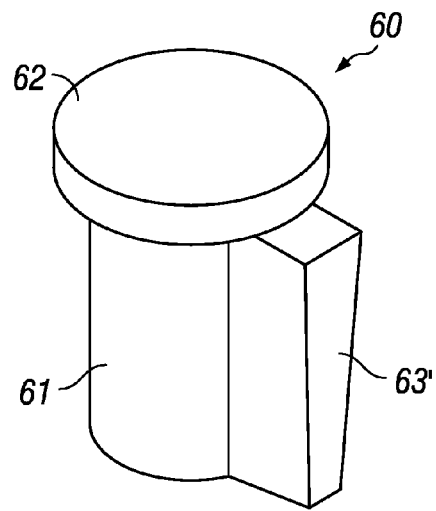
Figure 5B:
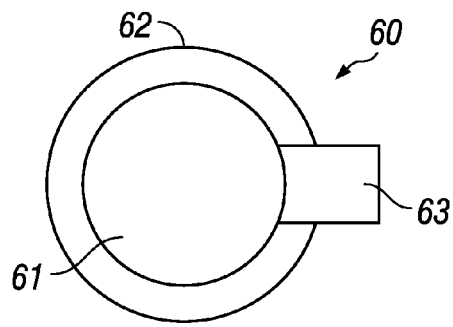
Figure 5E:
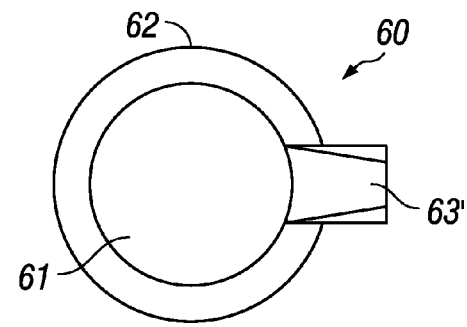
Figure 5C:
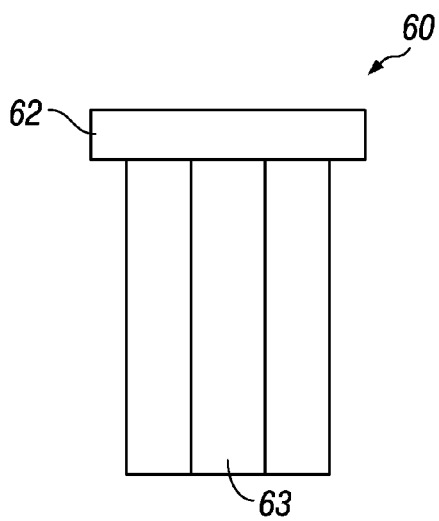

FIGS. 5A-5C depict perspective, bottom and side views of one embodiment of pin 60. In some embodiments, pin 60 may include central core 61. Central core 61 may have a diameter corresponding to the diameter of central passage 52 of resilient insert 50. When central core 61 is inserted in central passage 52 of resilient insert 50, pin 60 may inhibit resilient insert 50 from reducing in diameter. In some embodiments, if pin 60 is inserted into resilient insert 50 when resilient insert 50 is positioned in recessed portions 36, pin 60 may prevent resilient insert 50 from radially compressing.

In some embodiments, pin 60 may include radial extension 63. Radial extension 63 may extend along pin 60 parallel to the longitudinal axis of central core 61. In some embodiments, radial extension 63 may have a width corresponding to the width of slot 54 in resilient insert 50. In some embodiments, if pin 60 is inserted into resilient insert 50 when resilient insert 50 is positioned in recessed portions 36, radial extension 63 positioned in slot 54 may prevent resilient insert 50 from radially compressing.

Figure 5F:
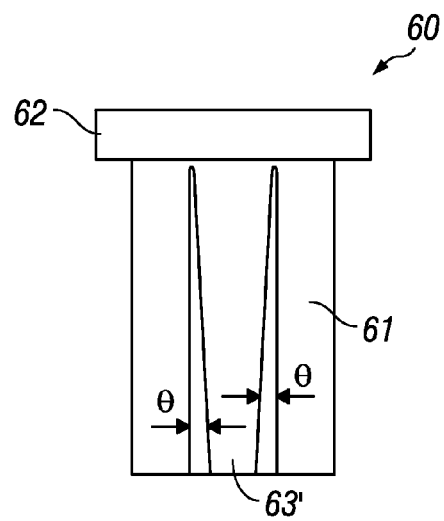

FIGS. 5D-F depict perspective, bottom and side views of one embodiment of pin 60 having a tapered radial extension 63' (i.e., angle θ). In some embodiments, tapered radial extension 63' may have a 5 degree taper. In some embodiments, the taper θ of pin 60 may be less than 3 degrees. Tapered radial extension 63' may reduce the effort needed to position pin 61 in resilient insert 50. A taper θ on radial extension 63' may be a curved taper or a straight taper.

FIGS. 6A-6C depict perspective and side exploded views of embodiments of a portion of spine stabilization system 100 prior to insertion of rod 10, resilient insert 50 and pin 60. In FIGS. 6A and 6B, embodiments are depicted in which bone fastener 20 is positioned in collar 30. In some embodiments, head 22 of bone fastener 20 may be pre-positioned in collar 30 with shank 24 extending out of second end 44. In some embodiments, bone fastener 20 may be top-loaded into collar 30. Bone fastener 20 may be advanced into channel 40 of collar 30 and pass through collar 30 until shank 24 extends from collar 30 and head 22 is positioned in cavity 46. Rod 10 may be advanced into channel 40. Resilient insert 50 may be advanced in arms 34 until ridge 56 seats in recessed portions 36. Pin 60 may be inserted in central passage 52 of resilient insert 50. In some embodiments, resilient insert 50 may be advanced into arms 30 without torque. A tool may be used to pull on collar 30 while a driver or other tool pushes on resilient insert 50.

In some embodiments, bone fastener 20 may be bottom-loaded into collar 30. FIG. 6C depicts one a side view depicting bone fastener 20 positioned for bottom-loading into collar 30. Bone fastener 20 may engage bone in a vertebral body. Collar 30 may be advanced onto bone fastener 20. Rod 10 may be inserted in channel 40 and seated on head 22 of bone fastener 20. Resilient insert 50 may be advanced in arms 34 until ridge 56 seats in recessed portions 36. Pin 60 may be inserted in central passage 52 of resilient insert 50.

FIG. 7 depicts a side view of one embodiment of a portion of spine stabilization system 100. As depicted in FIG. 7, once rod 10 has been positioned in channel 40, resilient insert 50 may be advanced into arms 34. In some embodiments, rod 10 may contact head 22 of bone fastener 20. Advancing resilient insert 50 into arms 34 may provisionally secure rod 10 in position until other bone fastener assemblies 15 can be positioned on other parts of the spine. In some embodiments, resilient insert 50 may be radially compressed and then inserted into arms 34. In some embodiments, advancing resilient insert 50 into channel 40 may radially compress resilient insert 50 when ridge 56 contacts arms 34. In some embodiments, once resilient insert 50 is positioned in recessed portions 36, bone fastener assembly 15 may be provisionally secured to rod 10. Provisionally securing bone fastener assembly 15 to rod 10 may allow a surgeon to move rod 10 cephalad and caudal, remove resilient insert 50 to bend rod 10 or make other adjustments, or secure other bone fastener assemblies 15 engaged in other vertebrae to rod 10 before securing spine stabilization system 100.

After rod 10 has been positioned in channel 40 of collar 30 and resilient insert 50 has been seated on rod 10, pin 60 may be advanced into resilient insert 50 to securely couple collar 30 to rod 10. FIGS. 8A and 8B depict side and top views of one embodiment of a portion of spine stabilization system 100 in which bone fastener assembly 15 is coupled to rod 10. Head 22 of bone fastener 20 may be positioned in collar 30. Rod 10 may be positioned in channel 40. Resilient insert 50 may be positioned in recessed portions 36 of collar 30 such that first resilient insert 50 is able to rotate radially relative to collar 30.

Bone fastener assemblies 15 may include, but are not limited to, collars 30, resilient inserts 50, pins 60 and bone fasteners 20. Bone fastener 20 may be advanced into a vertebral body by rotating bone fastener assembly 15 to engage threads 25 of bone fastener 20 with the bony tissue. In some embodiments, the central axis of collar 30 may be aligned with the longitudinal axis CY of bone fastener 20. Bone fastener 20 may be angulated in a symmetrical conical range of motion about the aligned axes. Bone fastener 20 may be constrained from motion outside a selected limit axis by contact between neck 23 of bone fastener 20 and collar 30. Alignment of the central axis CY of bone fastener 20 with the longitudinal axis of collar 30 may be considered a neutral position relative to the range of motion. The alignment is a neutral position because bone fastener 20 may be angulated an equal amount in any direction from the central axis of collar 30. When a driver is inserted into bone fastener 20, the longitudinal axis CY of bone fastener 20 may be substantially aligned with the central axis of collar 30 to facilitate insertion of bone fastener 20 into a vertebral body.

In some embodiments, the angle of the longitudinal axis of a first bone fastener assembly coupled to a first vertebra may differ from the angle of the central axis of a second bone fastener assembly coupled to a second vertebra. By rotating and selectively positioning collars 30, differences and variations in the angulation of bone fasteners 20 may be accommodated by collars 30.

Angulation of collars 30 may allow fine adjustment of engagement angles of bone fasteners 20. In addition, angulation of collars 30 may allow adjustment in the orientation of bone fasteners 20 in a sagittal plane (i.e., to conform to lordosis of a spine). In some embodiments, a flexible driver or a polyaxial driver (e.g., a driver with a universal joint) may be used to drive the heads of bone fasteners 20 from a position that is off-axis from the longitudinal axis of bone fasteners 20 to reduce the size of an opening of the body needed to implant embodiments disclosed herein.

Embodiments disclosed herein include spine stabilization systems that may be assembled without a threaded closure member. By advancing resilient inserts 50 into collars 30, rod 10 may be captured in channel 40.

FIGS. 8A and 8B depict end and top views of one embodiment of a portion of spine stabilization system 100 having bone fastener assembly 15 coupled to rod 10. In some embodiments, resilient insert 50 may be advanced into collar 30 until surface 53 of resilient insert 50 is below top surface 39 of collar 30. In some embodiments, resilient insert 50 may be advanced into collar 30 until top surface 53 (as shown in FIG. 4A) is even with top surface 39 of collar 30. Advancing resilient insert 50 until top surface 53 is at or below top surface 39 of collar 30 may provide a surgeon with visual or tactile cues that resilient insert 50 is securely coupled to collar 30. In some embodiments, the position of top surface 53 relative to surface 39 may be determined visually. In some embodiments, the position of top surface 53 relative to surface 39 may be determined by tactile sensation. By using tactile sensations, either directly or through a tool, a surgeon may still be sure the assembled spine stabilization system 100 is securely coupled. In some embodiments, resilient insert 50 may be advanced into collar 30 until rod 10 is below top surface 39 of collar 30.

Various instruments may be used in a minimally invasive procedure to form spinal stabilization system 100 in a patient. The instruments may include, but are not limited to, positioning needles, guide wires, dilators, bone awls, bone taps, sleeves, drivers, tissue wedges, elongated member length estimating tools, mallets, tissue retractors, and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, elongated members, and inserts.

Instruments used to install spinal stabilization system 100 may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

A targeting needle may be used to locate an entry point in a vertebral body for bone fastener 20 of bone fastener assembly 15. In some embodiments, the targeting needle may be a Jamshidi® bone marrow biopsy needle. A targeting needle may include an outer housing. The outer housing may include a hollow shaft and a handle. Scale markings printed, etched, or otherwise placed on the hollow shaft may be used to approximate a length of bone fastener 20 needed for a vertebra. The handle may provide a grip that allows a user to manipulate the targeting needle.

In some embodiments, a guide wire may be used to advance and/or position components at a placement site. The guide wire may be an 18-gauge K-wire. The guide wire may pass down a shaft of a targeting needle outer housing. A guide wire may be from about 15 cm to about 65 cm in length. In some embodiments, guide wires provided in an instrumentation set are about 46 cm in length. The length of a guide wire may allow a surgeon and/or assistants to hold at least one portion of the guide wire at all times when the guide wire is inserted into vertebral bone, even during insertion, use, and removal of instruments along a length of the guide wire. A guide wire that can be held continuously during a surgical procedure may inhibit removal or advancement of the guide wire from a desired position during a minimally invasive surgical procedure. A distal end of a guide wire may include a point, which may facilitate insertion of the distal end of the guide wire into vertebral bone. In some embodiments, a distal end of the guide wire may not be pointed. A position of an unpainted guide wire in bone may be easier to maintain during a spinal stabilization procedure.

Dilators may be used during a minimally invasive surgical procedure to push aside tissue and create space to access vertebral bone. In some embodiments, four tissue dilators of increasing diameter may be used to establish sufficient working space to accommodate instruments and spinal stabilization system components. In some embodiments, especially for a mid-vertebra or for mid-vertebrae of a multi-level stabilization system, only three dilators may be needed to form sufficient working space. Dilators in an instrumentation set may increase in diameter incrementally by a selected amount. For example, outside diameters of dilators in an instrumentation set may increase sequentially by increments of about 0.5 mm.

A bone awl may be used to breach cortical bone of a pedicle. A guide wire that is inserted in vertebral bone in a desired orientation may be inserted through a passage that extends through the bone awl. The bone awl may be moved down the guide wire so that the bone awl tip contacts the pedicle. The bone awl may have a length that allows a guide wire positioned in vertebral bone to always be held in at least one location when the guide wire is placed through a passage in the targeting needle.

During some surgical procedures downward force and some rotation of the bone awl may be sufficient to breach cortical of a vertebra. During some surgical procedures, an impact force may be needed for the bone awl to breach cortical bone. In some embodiments, a guide wire may be removed, the bone awl may be used to breach cortical bone, and the guide wire may be reinserted. In some embodiments, a small dilator may be placed over the portion of the guide wire extending from the bone awl so that a first end of the dilator contacts the bone awl. A mallet or other impact device may be used against a second end of the dilator so that the bone awl breaches cortical bone of the vertebra. The dilator may be removed from the bone awl and contact with the guide wire may be reestablished.

A bone tap may be used to form a threaded passage of a desired depth through a pedicle and into a vertebral body. The tap may have a passage so that the tap can be moved down the guide wire toward the bone.

A guide wire positioned in vertebral bone may be held near a top of a dilator inserted over the guide wire at a surgical site. A proximal end of the guide wire may be positioned through a distal end of a passage in the tap without a removable handle coupled to the shaft. A proximal portion of the guide wire may be held when the proximal portion of the guide wire extends beyond the top of the shaft. A portion of the guide wire may always be held during use of the tap. The shaft may be moved down the guide wire until the shaft contacts the vertebral bone.

A first reading of indicia relative to a proximal end of a dilator may be taken when a first flute is located at a pedicle. The tap may be rotated so that flutes form a threaded opening through the pedicle and into a vertebral body. The flutes may have a diameter that is about 0.1 mm to about 0.7 mm less than a maximum thread flight of a bone fastener to be positioned in the threaded opening formed by the flutes. In one embodiment, the tap may form a thread that is about 0.5 mm less than a maximum thread flight of a bone fastener to be positioned in the threaded opening formed by the flutes. A position of the tap may be monitored using a fluoroscope. When the threaded opening is formed to a desired depth, a second reading of indicia relative to the dilator may be taken. A length of a bone fastener to be inserted into the vertebral body may be estimated by taking the difference between the indicia readings. After a threaded opening is formed to a desired depth, the tap may be removed by rotating the tap until all the flutes are disengaged from the vertebral bone.

A detachable member may be used as a guide to install bone fasteners 20 of spine stabilization system 100 in vertebral bone. A detachable member may be coupled to bone fastener 20. A distal end of a detachable member may be tapered or angled to reduce bulk at a surgical site. A cross section transverse to a longitudinal axis of a detachable member may have shapes including, but not limited to, circular, ovoid, square, pentagonal, hexagonal, and combinations thereof. In some embodiments, a detachable member may be hollow. In some embodiments, a thickness of a hollow detachable member may be uniform. In some embodiments, a thickness of a hollow detachable member may vary along the length of the detachable member. A detachable member with a passage extending longitudinally from a first end of the detachable member to a second end of the detachable member may be referred to as a "sleeve".

Instruments may be inserted into the sleeve to manipulate bone fastener 20. Movement of the sleeve may alter an orientation of collar 30 relative to bone fastener 20 of spine stabilization system 100. In some embodiments, a sleeve may be used as a retractor during a spinal stabilization procedure.

A sleeve for a single-level vertebral stabilization system may include one or more channels in a wall of the sleeve to allow access to an adjacent vertebra. For some single-level vertebral stabilization procedures, only single-channel sleeves (i.e., sleeves with a single channel in a wall of the sleeve) may be used. For other single-level vertebral stabilization procedures, one or more multi-channel sleeves (i.e., sleeves with two or more channels in a wall of the sleeve) may be used. Channels may provide flexibility to or enhance flexibility of a multi-channel sleeve. In some embodiments, a proximal portion of a multi-channel sleeve may have a solid circumference. A region of solid circumference in a multi-channel sleeve may enhance stability of the multi-channel sleeve. In some embodiments, a multi-channel sleeve may be longer than a single-channel sleeve.

A sleeve used at a middle vertebra in a multi-level stabilization procedure may be a multi-channel sleeve. Channels in a multi-channel sleeve may allow access to adjacent vertebrae from a middle vertebra. A sleeve used at an end vertebra of a multi-level stabilization system may be a single-channel sleeve or a multi-channel sleeve. A system for coupling a bone fastener assembly to a multi-channel sleeve may include a limiter that inhibits spreading of arms of the sleeve to inhibit release of the bone fastener assembly from the sleeve.

A channel in a wall of a sleeve may allow access to a vertebra that is to be stabilized with a spinal stabilization system being formed. In some embodiments, a single-channel sleeve may be coupled to a bone fastener assembly to be inserted into vertebral bone of a first vertebra. The single-channel sleeve may allow access to a second vertebra from the first vertebra. In some embodiments, a multi-channel sleeve may be coupled to a bone fastener assembly to be inserted into vertebral bone of a first vertebra. The multi-channel sleeve may allow access from the first vertebra to adjacent vertebrae.

Instruments may access a spine stabilization system through a passage in a sleeve. In some embodiments, a channel in a wall of a sleeve may extend a full length of the sleeve. In some embodiments, especially in embodiments of multi-channel sleeves, a channel in a wall of a sleeve may extend only a portion of the length of the sleeve. In some embodiments, a channel in a wall of a sleeve may extend 25%, 50%, 75%, 80%, 90%, 95% or more of the length of the sleeve. A channel may extend to a distal end of a sleeve such that a rod inserted in the channel may pass from the sleeve into a channel of a collar of a bone fastener assembly coupled to the sleeve.

A channel in a sleeve may be any of a variety of shapes. A channel may have a width that exceeds a width (e.g., a diameter) of a rod that is to be inserted in the channel. In some embodiments, a channel may be a linear opening parallel to a longitudinal axis of the sleeve. In some embodiments, a channel may have a non-linear shape including, but not limited to, a helical pattern, an arc, an "L" shape, or an "S" shape. A non-linear channel may allow a rod to travel along a predetermined path. In some embodiments, adjacent sleeves may include channels with matching profiles, allowing ends of a rod to follow similar paths down the sleeve channels.

In some embodiments, a sleeve may be a multi-channel sleeve having walls forming a passage, and channels that extend from a distal end of the sleeve through a portion of the walls. Channels in the walls may allow instruments to be positioned and used to form a plane through soft tissue to one or more adjacent vertebrae. A rod may be inserted in the tissue plane and positioned in collars of bone fastener assemblies anchored in vertebrae and coupled to sleeves. A passage may allow instruments to be positioned and used to manipulate a bone fastener assembly that is coupled to a distal end of the sleeve. A distal end of a sleeve may include a flange that mates with a complementary flange on a collar of a bone fastener assembly. A distal end of a sleeve may be tapered to reduce bulk (e.g., reduce diameter) at a surgical site.

In some embodiments, a sleeve may be a single-channel sleeve for use in single-level or multi-level spinal stabilization procedures. A sleeve may be used at the outermost vertebrae to be stabilized during installation of a multi-level vertebral stabilization system. The sleeve may be coupled to a collar of a bone fastener assembly. Instruments may be inserted through a passage in the sleeve to access an anchored bone fastener assembly coupled to the sleeve. An instrument may be moved through a channel toward an adjacent vertebra to form a tissue plane in soft tissue between the sleeve and the adjacent vertebra.

A sleeve may be coupled to a bone fastener assembly in various ways to inhibit movement of the sleeve relative to a collar of the bone fastener assembly. A system used to couple the sleeve to the bone fastener assembly may inhibit rotation and translation of the sleeve relative to the collar.

A sleeve may be coupled to a collar of a bone fastener assembly in various ways. When a sleeve is coupled to a collar, rotation and translation of the sleeve relative to the collar may be inhibited. A system used to couple a sleeve and collar should be simple, inexpensive to implement, and should not significantly weaken the mechanical strength of the collar and/or the sleeve. Sleeves may be coupled to collars using various coupling systems including, but not limited to, flanges, threaded connections, interlocking connections (e.g., ratcheting connection systems), and/or interference fits.

In one embodiment of an interlocking connection system, a sleeve may include an opposing pair of deflectable arms. Each deflectable arm may include a tooth. The deflectable arms may be forced outwards during coupling of a collar to the sleeve. When the collar is coupled to the sleeve, the deflectable arms may be positioned in channels in the collar, with the teeth positioned in indentions in the collar. The presence of the deflectable arms in the channels of the collar may inhibit rotation and translation of the sleeve relative to the collar. Separation of the sleeve from the collar may be achieved by insertion of an expander in the sleeve. The expander may be used to force the deflectable arms outwards and expel the teeth from the indentions.

In some sleeve and collar coupling embodiments, the sleeve and the collar may include members that work together to inhibit radial expansion of walls of the sleeve. A stop in a sleeve and a ledge in a collar may be needed in a multi-channel sleeve embodiment. A stop in a sleeve and/or a ledge in a collar may not be needed in a single-channel sleeve embodiment or in a collar for single-level stabilization.

In some sleeve and collar coupling embodiments, a sleeve may include a protrusion that mates with a complementary groove in a collar. Alternatively, a sleeve may include a groove that mates with a complementary protrusion of a collar. Flange 35 of collar 30 may engage a complementary feature of a sleeve.

In some embodiments, a sleeve and/or a collar may include a locking system to inhibit rotation of the sleeve relative to the collar. The locking system may be, but is not limited to, threading, interference fits, frictional engagement, or a pressfit connection. In some embodiments, a locking system may inhibit translation and/or rotation of a sleeve relative to a collar. In one embodiment in which distal end portions of movable members in a sleeve are coupled to the collar, rotation and translation of the collar relative to the sleeve may be inhibited when distal end portions of the movable members are positioned in the openings.

In one embodiment, an inner sleeve may be positioned in a sleeve to inhibit translation and/or rotation of the sleeve relative to a collar of a bone fastener assembly. A distal end of inner the sleeve may contact an upper end of collar 30. A proximal portion of the inner sleeve may engage a proximal portion of the sleeve. The engagement may allow the inner sleeve to apply a force against collar 30 that presses a flange against a flange on the sleeve to inhibit translation of the sleeve relative to the collar. The engagement may be, but is not limited to, a threaded connection, an interference fit, a frictional fit, or a keyway type of connection.

In some embodiments, a distal end of an inner sleeve may be roughened or textured to frictionally engage a proximal surface of the collar. The frictional engagement may inhibit rotation of the sleeve relative to the collar.

In some embodiments, a sleeve may include a pair of hinged arms configured to couple to a collar. The arms may be pivotally coupled together by a hinge located near a proximal end of a sleeve. In some sleeve embodiments, a sleeve may include a locking element or a biasing element (e.g., a spring) near or at the hinge. A locking element or biasing element may cause a clamping force to be exerted on the collar to maintain the collar in the sleeve and/or to inhibit rotation of the collar in the sleeve.

In some sleeve embodiments, proximal portions of sleeves may be chamfered to allow ends of the sleeves to more closely approach each other than sleeves with a uniform cross section. Chamfered surfaces may reduce space between proximal ends of two sleeves. During some surgical procedures, only one of the sleeves may be chamfered. During some surgical procedures, the use of a sleeve with a chamfered surface may allow for a smaller incision than required when using non-chamfered sleeves. In some embodiments, other types of sleeves may be used to reduce space between proximal ends of sleeves. Other types of sleeves may include, but are not limited to, sleeves of different lengths, sleeves of different diameters, and sleeves with flexible end portions.

Sleeves may be of various lengths. Sleeves of different lengths may be used in the same surgical procedure. A sleeve length used in a spinal stabilization procedure may be determined by a patient's anatomy. Sleeves may be just short enough to allow manipulation by a medical practitioner above an incision in a patient. In some embodiments, sleeves may be about 3.5 to about 11.5 cm long. For example, a single-channel sleeve may be about 10 cm long. In some embodiments, sleeves may be about 11.5 cm to about 14 cm long. For example, a single-channel or a multi-channel sleeve may be about 12.5 cm long. A multi-channel sleeve may be longer than a single-channel sleeve. In some embodiments, a multi-channel sleeve may be at least about 15 cm long. For example, a multi-channel sleeve may be about 16 cm long. Sleeves that are too long may require a longer incision and/or a larger tissue plane for insertion of a spinal stabilization system. Insertion of a rod may be more difficult with sleeves that are longer than necessary. Sleeves with excess length may be bulky and hard to manipulate during a surgical procedure.

A sleeve may be flexible over its entire length or include a flexible portion near a proximal end of the sleeve. A flexible portion may allow positioning of a proximal portion of a sleeve in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

During some spinal stabilization procedures, a sleeve without a second portion that is able to move relative to a first portion may be used at one vertebra, and a sleeve with a second portion that is able to move relative to a first portion may be used at one or more vertebrae that are to be stabilized.

When bone fasteners of bone fastener assemblies are positioned in vertebral bone, sleeves coupled to collars of the bone fastener assemblies may be moved in desired positions. During surgery, a sleeve in a patient may be oriented towards an adjacent vertebra that is to be stabilized to reduce the required incision size. In some embodiments, channels of the sleeves may be aligned so that a rod may be advanced into channels in collars of the bone fastener assemblies. In some embodiments, multi-channel sleeves may be coupled to all three pedicles. In some embodiments, differently shaped sleeves (e.g., circular, oval) may be used in one or more of the pedicles. Channels of the sleeves may be aligned so that a rod may be moved down the sleeves and into channels into the collars of the bone fastener assemblies.

In some embodiments, channels of sleeves may face a direction other than toward each other. A rod may be curved in an appropriate shape to engage channels in the collars when the channels of the sleeves are angled. In some embodiments, channels in the sleeve may not be longitudinal channels down the length of the sleeve. In embodiments of sleeves with non-longitudinal channels, the channels of two adjacent sleeves may not face towards each other when the openings of collars coupled to the sleeves are aligned.

In one embodiment, a frame may couple to two or more sleeves. As used herein, a "frame" includes any of a variety of structural elements including, but not limited to, rods, bars, cages, or machined blocks. In some embodiments, a frame may provide a rigid coupling between two sleeves. In some embodiments, a frame may allow for angular or translational movement between sleeves. For example, in some embodiments a frame may include slidable elements that allow sleeves to be translated toward each other or away from each other to facilitate compression or distraction of vertebrae. In some embodiments, a frame may enable sleeves to pivot toward each other or away from each other. In some embodiments, a frame may allow for movement of sleeves to facilitate spinal reduction.

In some embodiments, after a bone fastener assembly is coupled to a sleeve, a driver may be coupled to a bone fastener of the bone fastener assembly. The driver may be used to insert the bone fastener into vertebral bone. In some embodiments, a driver may be positioned in a sleeve and coupled to bone fastener 20 and/or collar 30. Coupling the driver to collar 30 and to bone fastener 20 may ensure proper alignment of the driver relative to bone fastener 20. Coupling the driver to collar 30 and to bone fastener 20 may also inhibit movement of collar 30 relative to bone fastener 20 during insertion of bone fastener 20. The driver may couple to flange 35, arm 34 or some other portion of first end 32 or second end 44.

A driver may be positioned in a passage in a sleeve and coupled to a bone fastener during use. The driver may be rotatable relative to the sleeve so that a bone fastener can be inserted into vertebral bone. In some embodiments, clearance between the driver and the sleeve may be relatively small. In some embodiments, the clearance between the driver and the sleeve may range from about 0.1 mm to about 0.75 mm. For example, the clearance between the driver and the sleeve may be about 0.25 mm (i.e., an inner diameter of the sleeve may be about 0.5 mm greater than an outer diameter of the driver). Also, clearance between a sleeve and a dilator may be relatively small. The small clearances may inhibit undesired movement of the instruments relative to each other and/or reduce bulkiness at the surgical site.

During a minimally invasive surgical procedure, a plane may be created in tissue from a first vertebra to a second vertebra. A rod may be positioned in the plane during the surgical procedure. In some embodiments, a tissue plane may be formed using a targeting needle. The targeting needle may be positioned at the first vertebra. The distal end of the needle may be moved toward the second vertebra to form the plane while maintaining a position of the needle at a surface of the skin. The needle may be moved back and forth a number of times to clearly establish the plane. Care may need to be taken to avoid bending the targeting needle during establishment of the plane.

In some embodiments, a tissue wedge may be used to form a plane in tissue between a first vertebra and a second vertebra. A blade used in a wedge may be a double-wedged blade, may have a diamond-like shape, may have blunt edges to avoid severing tissue during use of the tissue wedge, or the like. The distal end of a blade may be rounded. A shape of the distal end may inhibit damage to tissue and may facilitate movement of the blade towards a target location during formation of a plane in tissue between vertebrae. In some tissue wedge embodiments, a tissue wedge may include a hook. A cutting edge in the hook may be used to sever portions of tissue (e.g., fascia) through which a blade cannot form a plane. A cutting edge may be oriented in the blade so that severing of tissue results when the tissue wedge is pulled away from the spine.

An estimating tool may be used to estimate a distance between bone fastener assemblies anchored in vertebrae. The bone fastener assemblies may be part of a single-level or multi-level spinal stabilization system. The distance estimated by an estimating tool may be used to determine a desired length of a rod to be coupled to the anchored bone fastener assemblies. An estimating tool may be designed such that a maximum separation distance exceeds an expected distance between anchored bone fastener assemblies. Fully extended arms may be manually compressed and inserted into passages of sleeves coupled to anchored bone fastener assemblies. For a multi-level system, the arms may be inserted in sleeves coupled to the outermost bone fastener assemblies while one or more sleeves coupled to one or more inner vertebrae are held out of the way.

An estimating tool may be advanced toward anchored bone fastener assemblies. In some embodiments, an estimating tool may be advanced toward the anchored bone fastener assemblies until members of the estimating tool contact collars and/or bone fasteners of the bone fastener assemblies. With the estimating tool contacting collars and/or bone fasteners, an activator of the estimating tool may be engaged. Engaging an activator of an estimating tool may limit the biasing element such that the distance between the members of the estimating tool does not exceed the distance between the anchored bone fastener assemblies. With the activator engaged and the distance between the members of the estimating tool fixed to indicate the distance between the anchored bone fastener assemblies, the estimating tool may be moved upwards to remove the estimating tool from the patient. When the estimating tool is moved upwards, arms may compress to facilitate removal of the estimating tool from the sleeves.

Once removed from the sleeves, the biasing element may restore the distance between the members of the estimating tool to indicate the separation between anchored bone fastener assemblies 15. The distance between the members of the estimating tool may be used to estimate a length of rod 10 needed to couple the anchored bone fastener assemblies 15. The distance may be read using a scale provided in the instrumentation kit. In some embodiments, the scale may be indicia or etching on a surface of the instrumentation kit. In one embodiment, a length of rod 10 may be chosen to allow for bending of rod 10 and/or to allow rod 10 to extend beyond collars 30 of the anchored bone fastener assemblies 15. For example, 15 mm may be added to the distance between the members of the estimating tool. In some embodiments, a length of rod 10 may be chosen such that rod 10 extends 2 mm or more beyond collars 30. In some embodiments, a length of rod 10 may be chosen such that ends of rod 10 do not extend from collars 30.

In some embodiments, an estimating tool may include a gage having arms for providing an estimate of the distance between sleeves. Thus, with the arms of the estimating tool positioned together, the gage may have or may be set to a zero reading. With the arms extended to meet resistance in the sleeves, the gage may provide an estimate of the distance between the sleeves. The distance between the sleeves may be used to estimate a length of rod 10 needed to couple the anchored bone fastener assemblies. In one embodiment, a length of rod 10 may be chosen to be greater than the distance measured by a gage to allow rod 10 to extend beyond slots of collars 30 of anchored bone fastener assemblies 15.

In some embodiments, a rod positioner may be used to guide rod 10 through one or more sleeves coupled to bone fastener assemblies 15 and to position rod 10 in channels 40 in collars 30 proximate pedicles of vertebrae. A rod positioner may include an outer shaft, a handle, an inner shaft, and a grasping member. In some embodiments, the grasping member may be a hook. A first end (i.e., proximal end) of the outer shaft may be connected to the handle. A second end (i.e., distal end) of the outer shaft may be coupled to the grasping member. The inner shaft may pass through the handle and the outer shaft. A second end (i.e., a distal end) of the inner shaft may contact rod 10 positioned in the grasping member. A first end (i.e., proximal end) of the inner shaft may extend from the handle. The proximal end of the inner shaft may be a knob or a thumb plate. An amount of force applied to a rod positioned between the grasping member and the distal end of the inner shaft may be controlled by the amount of pressure applied to the proximal end of the inner shaft. Pressure may be applied to the proximal end of the inner shaft manually or mechanically. Mechanical means of applying pressure to the proximal end of the inner shaft include, but are not limited to, forceps handles and an adjustable rotor. The distal end of the inner shaft may be positioned proximate a grasping member. Rod 10 may be positioned between the grasping member and the distal end of the inner shaft of the positioning tool before or after initial insertion of rod 10 into a sleeve. Rod 10 may be held between the grasping member and the distal end of the inner shaft with pressure applied to the proximal end of the inner shaft. The distal end of the inner shaft may be contoured (e.g., curved) to allow some motion (e.g., rocking motion) of rod 10 while rod 10 is coaxed into position. During some installation procedures, a positioning tool may remain coupled to rod 10 until resilient inserts 50 or pins 60 are secured in collars 30 of anchored bone fastener assemblies 15. In some cases, pressure supplied to rod 10 with a rod positioner may not be sufficient to seat rod 10 in channel 40 in collar 30. A seater may be used in conjunction with a rod positioner to maneuver rod 10 into one or more channels 40 in collars 30. During some procedures, a rod positioner may be removed from rod 10 before using the seater.

After rod 10 has been positioned and seated in channels 40 as desired, resilient inserts 50 may be advanced into collars 30 to secure rod 10 to collars 30. A tool may connect to resilient insert 50. In some embodiments, the tool may reduce the radius of curvature of resilient insert 50 to less than the width of channel 40. In some embodiments, a first tool may reduce the radius of curvature of resilient insert 50 to less than the width of channel 40 and a second tool may advance the reduced resilient insert 50 into channel 40.

After resilient insert 50 is positioned in recessed portions 36, pin 60 may be inserted into resilient insert 50 such that resilient insert 50 is prevented from reducing the radius of curvature. A tool may engage pin 60. A tool used to insert resilient insert 50 may be used to guide or insert pin 60 into resilient insert 50. Once pin 60 is seated in resilient insert 50, resilient insert 50 may be inhibited from reducing its radius of curvature unless pin 60 is removed. A tool may be used to expand the width of channel 40 to facilitate insertion of pin 60. Pin 60 may inhibit resilient insert 50 from reducing its radius of curvature. Pin 60 may increase the radius of curvature of resilient insert 50. Pin 60 may be advanced into the patient, to the implantation site, or into resilient insert 50 via a guide wire.

In some embodiments, advancement of pin 60 into resilient insert 50 or withdrawal of pin 60 from resilient insert 50 may be accomplished using only compressive or tensile forces. For example, in some embodiments, pin 60 may be inserted into resilient insert 50 by pushing down on pin 60 positioned in central passage 52 of resilient insert 50. Insertion may be facilitated by pulling up on flanges 35 on collar 30. In some embodiments, removal may be accomplished by pushing down on flanges 35 and pulling up on cap 61. The application of torques to either resilient insert 50 or pin 60 may not be necessary.

Minimally invasive procedures may involve locating a surgical site and a position for a single skin incision to access the surgical site. The incision may be located above and between (e.g., centrally between) vertebrae to be stabilized. An opening under the skin may be enlarged to exceed the size of the skin incision. Movement and/or stretching of the incision, bending of a rod, and angulation of collars of bone fastener assemblies may allow the length of the incision and/or the area of a tissue plane to be minimized. In some embodiments, minimally invasive insertion of a spinal stabilization system may not be visualized. In some embodiments, insertion of a spinal stabilization system may be a top-loading, mini-opening, muscle-splitting, screw fixation technique.

Insertion of a spinal stabilization system may include gradually increasing the diameter of an opening formed in a pedicle and/or vertebral body to accept a bone fastener assembly. For example, a targeting needle may have outer diameter of about D. A bone awl inserted after the targeting needle may have an outer diameter incrementally larger than the outer diameter of the targeting needle. As used herein, an incrementally larger diameter may be large enough to allow a snug but adjustable fit. For example, the bone awl may have outer diameter of about (D+x). A tap portion of a bone tap inserted after the bone awl may have a minor diameter of about (D+2x). A bone fastener may have a minor diameter of about (D+3x). In some embodiments, x may be between about 0.1 mm and about 1.0 mm. For example, x may be about 0.5 mm. Incremental sizing of the targeting needle, bone awl, tap, and bone fastener may promote a proper fit of the bone fastener in the vertebra to be stabilized.

In one embodiment of a spinal stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of pedicle anatomy during the procedure. The arm should be rotated through a full range of motion prior to beginning the procedure to ensure that there is no obstruction or radio-opaque object in the way. The fluoroscope may be positioned so that Ferguson views and "bullseye" views are obtainable. Once the patient is positioned and the ability to obtain fluoroscopic images of the target levels for instrumentation has been confirmed, the patient may be prepared and draped sterilely.

For most of the lumbar region, the vertebral pedicle is an obliquely oriented cylindrical corridor. The angulation varies by approximately 5 degrees per level (e.g., L1: 5 degrees; L5: 25 degrees). A pre-operative fine-cut computed tomography image may be examined to determine any unique anatomy of the patient. Acquiring the pedicle in the most lateral and superior quadrant of the pedicle may be desirable to avoid the overriding facet during a minimally invasive procedure. A lateral entry point may allow for better screw convergence as well as less interference with the superior adjacent level facet joint. A targeting needle may be passed in a medial and inferior trajectory, thus following the natural pathway of the pedicle. Frequent fluoroscopic inspection in both an anteroposterior and lateral plane may ensure proper passage of the needle as the needle is inserted into vertebral bone.

Various techniques may be used to plan the skin incisions and entry points. In one embodiment, the planning sequence for a single-level stabilization may include the following four steps. First, an anteroposterior image may be obtained with the spinous processes centered at the target vertebral bodies. Vertical lines passing through midpoints of pedicles that are to receive bone fasteners may be marked on the patient. The lines do not represent skin entry points. The lines are markers of pedicle entry points used to estimate angles at which targeting needles to be inserted to contact the pedicles. In some embodiments, sets of vertical lines may be drawn corresponding to the lateral edges of the pedicles instead of lines corresponding to the midpoints of the pedicles.

Second, horizontal lines may be marked approximately through the centers of the pedicles (mid-pedicle lines) on the patient. In some embodiments, the lines may be drawn on the superior side of the center axes (superior to the mid-pedicle).

Third, an oblique or "bullseye" view (i.e., down a longitudinal axis of a pedicle) may be obtained on each side of the patient for each pedicle that is to be stabilized. Vertical oblique view lines may be marked on the skin at the midpoints of each of the pedicles that are to receive a bone fastener. The oblique view lines may be drawn in a different color than the vertical lines drawn during the first step. In some embodiments, vertical lines may be drawn corresponding to the lateral edges of the pedicles instead of lines corresponding to the midpoints of the pedicles.

The oblique view lines may be about 2 cm to about 3 cm away from the lateral pedicle border lines marked in the first step. For larger patients, the oblique view line may be greater than about 3 cm away from the midline marked in the first step. For smaller patients, the oblique view line may be closer than about 2 cm away from the midline marked in the first step. The intersection of the oblique view lines with the horizontal lines drawn in the second step may represent skin entry points for a targeting needle as the targeting needle passes through soft tissue at an angle towards the bony pedicle entry point. A side fluoroscopic image, the horizontal lines, and the vertical lines may help the surgeon triangulate between the skin entry points and bony entry points.

Fourth, an incision may be made in the skin between mid-pedicle lines along the vertical oblique view lines. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:200,000 epinephrine. To blunt the pain response, a long spinal needle may be used to dock on the bone entry point and inject the planned muscle path in a retrograde fashion as well. Once the incision has been made, tissue surrounding the incision may be pulled and/or stretched to allow access to a target location in a vertebra.

After sterile preparation and draping, the pedicle entry points may be fluoroscopically rechecked to ensure that the previously marked lines correspond to the intersection of the midline of the transverse process and the lateral joint and pars interarticularis. The intersection of the facet and the transverse process provides a starting point that may help avoid the canal and follow the natural inclination of lumbar pedicles. For the spinal stabilization system described, in which sleeves coupled to bone fastener assemblies are substantially unconstrained by insertion angles of the bone fasteners, patient anatomy may determine the most advantageous insertion angles of the bone fasteners.

A scalpel may be used to make a stab wound at the junction of an oblique view line and a mid-pedicle line. In one embodiment, the scalpel may be a #11 scalpel. A targeting needle may be passed through the incision in an oblique lateral to medial trajectory towards the bony entry point defined by a lateral pedicle border line. The C-arm of the fluoroscope may be placed in an anteroposterior position for this maneuver.

As the targeting needle encounters the bony anatomy, anteroposterior fluoroscopic images may be used to place the tip of the needle at the upper outer quadrant of the pedicle. In some embodiments, the needle may be walked medially along the transverse process to the pedicle entry point. In some embodiments, the needle tip may be docked by lightly tapping the tip into the bone with a mallet or other impact device to drive the tip into the bone. In some embodiments, the needle tip may be docked by applying downward pressure to the targeting needle to force the tip into the bone.

The fluoroscope may then be moved to a lateral position. The surgeon may correct the sagittal trajectory of the needle by moving the needle in an anterior or posterior direction to match the vector of the pedicle corridor. In some embodiments, a mallet or other impact device may be used to gently advance the targeting needle into the pedicle halfway to the pedicle-vertebral body junction. In some embodiments, force may be applied to the targeting needle to drive the targeting needle into the pedicle halfway to the pedicle-vertebral body junction. An anteroposterior image may then be obtained to confirm that the needle is approximately halfway across the pedicle in the anteroposterior view. If the tip is more than halfway across the pedicle in a lateral to medial projection, the trajectory may be too medial. Further advancement of the needle may risk passing the needle through the spinal canal.

The needle may be repositioned. A new starting point or new trajectory may be obtained. If the anteroposterior image demonstrates that the needle is significantly lateral in the pedicle, then the needle may have passed along the lateral portion of the pedicle. A needle that has passed along the lateral portion of the pedicle may be withdrawn and repositioned.

Once a proper trajectory has been obtained, the targeting needle may be advanced using a mallet. In some embodiments, the needle may be pushed in without a mallet. The targeting needle may be advanced to the junction of the pedicle and vertebral body under lateral fluoroscopic guidance. At this point, confirmation of position and trajectory can be repeated under anteroposterior fluoroscopy. A scale on the targeting needle may be used to approximate a length of a bone fastener to be used. A first depth of the targeting needle may be measured relative to a body surface when a pedicle is first encountered. A second depth of the targeting needle may be measured relative to the body surface after the targeting needle has been advanced to the desired depth in the vertebral body. An approximate length of the bone fastener to be used may be determined by taking a difference between the depth measurements.

After the targeting needle is in a proper position, a guide wire may be placed through a passage in the targeting needle into the vertebral body. Lateral fluoroscopic images may be obtained to indicate the position of the guide wire. In some embodiments, a small diameter tissue dilator may be placed over the guide wire and positioned on an upper surface of the targeting needle. The tissue dilator may provide stability to the guide wire. Added stability from the dilator may allow the guide wire to be successfully tapped into the vertebral body with a small mallet. Care should be taken to avoid kinking the guide wire.

Once the guide wire has been passed through the targeting needle and the targeting needle has been removed, the guide wire may be used as a guide to position one or more successively sized dilators around a target location in a pedicle. A dilator may be a conduit with a regular shape (e.g., cylindrical) or an irregular shape (e.g., C-shaped). A dilator may form an opening through soft tissue to the pedicle. For patients with a thick fascia, it may be advantageous to make a nick in the fascia with a scalpel blade to facilitate passage of the dilators. The dilators may be passed sequentially over the guide wire. The dilators may be rotated during insertion to facilitate dilation of surrounding tissue. The dilators may be inserted until the leading edges contact the pedicle. A distal end of a dilator may be tapered to facilitate positioning of the dilator proximate the pedicle. An instrumentation set for a spinal stabilization system may include two, three, four, or more successively sized dilators.

As used herein, "an inner diameter just slightly larger than an outer diameter" may mean that the inner diameter is between about 0.03 mm and about 1.0 mm greater than the outer diameter. For example, an inner diameter of a first dilator may be about 0.5 mm greater than the outer diameter of the guide wire. Lengths of dilators in a successively sized set may decrease with increasing diameter to facilitate removal of the smaller dilators. Care should be taken to avoid dislodging the guide wire during insertion and removal of the dilators.

After tissue dilation has been achieved, a large diameter dilator may be used to guide bone fastener assembly 15 including bone fastener 20, and collar 30 and/or insertion instruments toward a target location in a pedicle. In some embodiments, a pedicle may be prepared for receiving a bone fastener assembly. A bone awl may be positioned such that a tip of the bone awl is on or near a surface of a pedicle. The bone awl may be driven downwards into the pedicle to breach cortical bone of the pedicle. After the pedicle is breached, the bone awl may be removed from the patient. In some embodiments, an initial passage may be formed in the pedicle and the vertebral body using a drill or a drill and tap combination. A tap may be rotated to form a threaded passage through a pedicle and into a vertebral body to a desired depth. In some embodiments, a length of the threaded portion of a tap may be used to determine a depth of a threaded passage formed in a bone. For a threaded portion of a known length (e.g., 30 mm, 45 mm, 60 mm), a scaled image (e.g., X-ray image) of a depth of the threaded portion in a bone monitored during tapping may allow a medical practitioner to determine the depth of the threaded passage. In some embodiments, a tap may form threads of major diameter about 0.5 mm smaller than a major diameter of threads of bone fastener 20 to be inserted into the threaded passage.

In some embodiments, bone fastener assembly 15 with bone fastener 20 of an appropriate length may be selected for insertion in a patient. The size of bone fastener 20 may be verified with measurement indicia in an instrumentation set. In some embodiments, measurement indicia may be etched or printed on a portion of an instrumentation set. For example, the chosen bone fastener embodiment may be placed over the outline of bone fastener 20 embodiment printed on a tray of the instrumentation set.

The chosen bone fastener assembly 15 may be attached to a tool. In one embodiment, the tool may be rotated on flange 35 of collar 30 a sleeve (not shown). A driver may be used to extend the movable members to couple with collar 30. When bone fastener assembly 15 is coupled to the sleeve, a driver may be coupled to bone fastener 20. A shaft of the driver may be positioned in the passage of the sleeve. A removable handle may be attached to the shaft of the driver. The sleeve, collar 30 and bone fastener 20 may be substantially co-axial when the fastener driver is positioned in the sleeve. In some embodiments, the removable handle may be attached to the shaft of the driver after the bone fastener 20, collar 30, sleeve, and fastener driver combination is positioned down a guide wire through a dilator and against a pedicle.

After insertion of bone fastener assembly 15, a sleeve, and a driver in a dilator, the driver may be rotated to thread bone fastener 20 into the pedicle and vertebral body. Bone fastener 20 may be advanced into the pedicle under fluoroscopic guidance to inhibit breaching of the pedicle walls. When the tip of bone fastener 20 advances beyond the posterior margin of the vertebral body, the guide wire may be removed to inhibit inadvertent bending of the guide wire or unwanted advancement of the guide wire. Bone fastener 20 may be advanced to the facet joint. Bone fastener 20 may then be backed off about a quarter of a turn. Backing bone fastener 20 off about a quarter of a turn may allow for full motion of collar 30 relative to bone fastener 20. After bone fastener 20 has been advanced to the desired depth, the driver may be removed from the head of bone fastener 20 and from the patient.

After bone fastener 20 has been secured to the vertebra and the driver has been removed from the sleeve, the polyaxial nature of collar 30 coupled to bone fastener 20 may allow angulation of the sleeve relative to bone fastener 20. Tissue surrounding the incision may be released such that the sleeve is angled toward a central location between vertebrae to be stabilized. The sleeve may be moved to facilitate positioning of instruments and/or to facilitate access to the adjacent vertebra that is to be stabilized. For example, the sleeve may be tilted towards the adjacent pedicle so that additional length of an opening in the patient is not needed. The channel in the sleeve may be turned toward the adjacent pedicle that is to be stabilized with the spinal stabilization system being formed.

A plane of dilated tissue may be created between a first pedicle and a second pedicle to be stabilized with a spinal stabilization system. A first bone fastener assembly 15 and a sleeve may be coupled to the first pedicle. The second pedicle may be adjacent to the first pedicle. In one embodiment, a tissue wedge may be placed in the sleeve coupled to the first pedicle such that the distal end of the tissue wedge contacts head 22 of bone fastener 20. The proximal end of the sleeve coupled to the first pedicle may be held such that tissue around the incision is not pulled or stretched. The tissue wedge may be wanded through the channel in the sleeve and channels 40 in collar 30 toward the target location at the second pedicle, thereby creating a plane in muscle and other tissue between the head 22 of the installed bone fastener 20 and the target location of a second bone fastener 20. In some embodiments, a tissue wedge may be pivoted about an inside proximal edge of the sleeve such that the distal end of the tissue wedge bluntly splits the muscle and fascia along fibers and create a tissue plane between the two pedicles. The wanding action may be repeated more than once (e.g., two or three times) to create a good working plane and displace unwanted tissue from the plane. The wanding may create a tissue plane. In some embodiments, the tissue plane may be substantially trapezoidal. In some embodiments, a tissue plane may be created before bone fastener assembly 15 is inserted into a vertebra.

A tissue plane may be made in a variety of shapes including, but not limited to, substantially trapezoidal, substantially rhomboidal, and substantially triangular. A tissue plane with a substantially geometric shape may have the basic geometric shape with, for example, slightly curved edges and/or slightly rounded corners or apices. In some embodiments, a sleeve length may be chosen to reduce a size of a tissue plane that needs to be formed between pedicles. In some embodiments, creating a trapezoidal tissue plane may reduce the invasiveness of a procedure. Limiting the area of the plane may promote a faster recovery time and/or may reduce an amount of post-operative pain experienced by the patient.

In one embodiment, a tissue wedge may be coupled to a portion of a sleeve to facilitate creation of a tissue plane. In one embodiment, two pedicles may be targeted and bone fastener assemblies 15 may be anchored in both pedicles before creation of a tissue plane. A tissue wedge may be inserted at either of the pedicles. In some embodiments, the sleeves may be coupled to each other at proximal ends of the sleeves. The tissue wedge may be coupled to a sleeve and the sleeve may be used as an anchor during wending. Insertion of a rod into collars 30 of bone fastener assemblies 15, however, may require cutting of some tissue between the two sleeves. Other procedures may be used to create a tissue plane. For example, before targeting pedicle locations (i.e., before bone fastener insertion), a tissue wedge may be worked downward from an incision to create a tissue plane. Alternatively, a scalpel may be used to cut from the surface of the body to vertebral bone. Extensive use of a scalpel, however, may remove benefits of a minimally invasive procedure.

In one embodiment, a targeting needle may be passed through the tissue to create a tissue plane for insertion of rod 10. Once a well-defined tissue plane has been formed, a targeting needle may be passed down a first sleeve coupled to a first vertebra and then wanded along the formed plane over to a target location at a second pedicle. The target location at the second pedicle may be fluoroscopically confirmed. Bone fastener assembly 15 coupled to a sleeve may be secured in the second pedicle using a procedure similar to the procedure used to insert bone fastener assembly 15 in a first pedicle.

With bone fastener assemblies 15 secured in the vertebral bodies, sleeves coupled to bone fastener assemblies 15 may be oriented to facilitate insertion of rod 10 in the sleeves. In some embodiments, sleeves may serve as tissue retractors during a spinal stabilization procedure. Angular motion of a collar may be limited by a range of motion allowed between collar 30 and bone fastener 20 to which collar 30 is anchored. Angular motion of collar 30 may be limited by patient anatomy. Angular motion or orientation of one collar 30 or sleeve, however, may not depend upon a position of another collar 30 or sleeve. In some embodiments, channel openings in the sleeves may face each other. In some embodiments, channel openings in the sleeves may be angled relative to each other in various arrangements. A distance between the sleeves may be estimated using an estimating tool. The distance between the sleeves may be used to select a length of rod 10 needed to couple collars 30.

In one embodiment, flexible arms of an estimating tool may be positioned in sleeves. With the activator disengaged, the estimating tool may be advanced toward the pedicles until the arms or members rest on collars 30 or bone fasteners 20 of bone fastener assemblies 15. The activator may be engaged. When the arms are withdrawn from the sleeves, a biasing element may allow the arms to extend to the length indicative of the distance between bone fastener assemblies 15. A length of rod 10 may be selected by measuring a distance between the members of the estimating tool. The measured distance may be increased by an amount to allow rod 10 to extend beyond collars 30 after curvature and/or insertion. In one embodiment, about 5 mm to about 30 mm (e.g., about 15 mm) may be added to the measured distance. In some embodiments, a desired length of rod 10 may be a length that allows rod 10 to extend from each collar 30 by about 2 mm or about 3 mm. In some embodiments, ends of rod 10 may be flush with the outer surface of one or more collars 30.

In one embodiment, rod 10 of desired length may be chosen by estimating a distance between the sleeves without the use of an estimating tool. The sleeves may be positioned as desired (e.g., substantially parallel to each other). A distance between the most distant outer edges of the sleeves may be estimated. The estimated distance may be increased by an amount to allow rod 10 to extend beyond collars 30 after insertion. In some embodiments, from about 1 mm to about 20 mm may be added to the estimated distance. In some embodiments, a desired length of rod 10 may be a length that allows rod 10 to extend from each collar 30 by about 2 mm.

Rod 10 may be cut to length and contoured as desired. For example, a medical practitioner may use experience and judgment to determine curvature of a rod for a patient. A desired curvature for rod 10 may be determined using fluoroscopic imaging. In some embodiments, a curvature of rod 10 may be chosen such that, when rod 10 is secured to collars 30 of bone fastener assemblies 15, sleeves coupled to bone fastener assemblies 15 cross at a surface of the skin. Crossing of the sleeves at a surface of the skin allows the medical practitioner to minimize trauma to a patient by minimizing incision length and tissue plane area. Rod 10 may be bent or shaped with a tool (e.g., a rod bender) to allow insertion of rod 10 through channels of sleeves with various spatial locations and/or various angular orientations.

Rods 10 may have shapes including, but not limited to, straight, bent, curved, s-shaped, and z-shaped. In some embodiments, rods 10 may have a substantially circular longitudinal cross section. In some embodiments, rods 10 may have other cross-sectional shapes including, but not limited to, regular shapes (oval, rectangular, rhomboidal, square) and irregular shapes. An instrumentation kit for a spinal stabilization system may include straight rods 10 and/or pre-shaped rods 10. Straight rods 10 and/or pre-shaped rods 10 may be contoured to accommodate patient anatomy if needed during the surgical procedure.

Channels of the sleeves and channels 40 of collars 30 may be oriented by rotating the sleeves to accommodate insertion and seating of rod 10. In some embodiments, a channel opening in a sleeve may be non-linear (e.g., bent, curved, or angled) to allow portions of the spine to be selectively stabilized. Sleeve orientation and/or design may be chosen to allow compression, distraction, and/or reduction of vertebrae. In some embodiments, there may be no constraints governing relative location and/or orientation of the sleeves. Sleeves may be forced apart or angled toward each other or away from each other to accommodate insertion of rod 10.

Prior to insertion of rod 10, the tissue wedge or targeting needle may be used to wand between bone fasteners 20 to ensure a clean plane between bone fasteners 20. An end of rod 10 may be inserted at an angle or substantially longitudinally in a passage and/or channel of a sleeve coupled to bone fastener assembly 15. Inserting rod 10 at an angle or substantially longitudinally allows the length of the incision and/or the area of the tissue plane to remain advantageously small. In some embodiments, sleeves coupled to anchored bone fastener assemblies may remain essentially unconstrained relative to each other during insertion of rod 10. In some embodiments, angular orientation of collars 30 may determine a trajectory of the rod down the sleeves and into collars 30 of bone fastener assemblies 15. Inserting rod 10 down two or more sleeves and through an open path (i.e., the tissue plane) may allow a medical practitioner to avoid surgical difficulties associated with anatomical abnormalities and/or misalignment of system components (e.g., in multi-level stabilization procedures).

Insertion of rod 10 may not be visualized subcutaneously. Therefore, a positioning tool may be used to guide rod 10 down the sleeves into channels 40 in collars 30. A distal portion of the positioning tool may be contoured. The contour may allow for some rotation of rod 10. With slight pressure, rod 10 may be rotated subcutaneously into a substantially horizontal position and seated in the collars. The positioning tool may be held firmly while still allowing a rocking movement between rod 10 and the distal end of the positioning tool. Movement of rod 10 may allow rod 10 to be maneuvered down the sleeves and into collars 30.

Channels 40 in collars 30 may be aligned with channels of sleeves to allow rod 10 to be positioned in collars 30. A positioning tool may be used to angle rod 10 through channels 40 such that an end of rod 10 protrudes through collar 30. With one end of rod 10 extending through first channel 40 in a first collar 30, the positioning tool may be used to seat the second end of rod 10 in a second collar 30 and translate rod 10 to a desired location relative to collars 30. The distal end of the positioning tool inner shaft may be contoured (e.g., curved and/or grooved) to allow some motion (e.g., rocking) of rod 10 while rod 10 is coaxed into position and/or rotated subcutaneously with the positioning tool. Pressure may be applied to the inner shaft to seat rod 10 in channel 40 of cylindrical collar 30.

In some embodiments, a seater may be used to seat rod 10 in the collars. In some embodiments, a seater may be used to push rod 10 into channels 40 in collars 30 while the positioning tool is used to maneuver rod 10 into place. Once rod 10 is positioned in collar 30, fluoroscopic confirmation may ensure that rod 10 is inserted fully into each collar 30. Prior to securing rod 10 in collars 30, rod 10 may be gripped firmly with the positioning tool and persuaded cephalad or caudad as needed. With rod 10 seated in collars 30, orientation of the sleeves may be constrained relative to each other.

After rod 10 is seated in collar 30, resilient insert 50 may be advanced into collar 30. Advancing resilient insert 50 into collar 30 may be performed by radially compressing resilient insert 50 and advancing resilient insert 50 into arms 34 and continuing to advance resilient insert 50 into recessed portions 36. Advancing resilient insert 50 into collar 30 may be performed by radially compressing resilient insert 50 and advancing resilient insert 50 into indentations 37 and continuing to advance resilient insert 50 into recessed portions 36 in arms 34.

In some embodiments, resilient insert 50 may be inserted into arms 34 using a slight twisting to reduce friction or otherwise facilitate insertion. Slight twisting of resilient insert 50 may be enough to avoid static friction and the associated torque. An advantage to embodiments disclosed herein may be the absence or reduction of torques applied to spine stabilization system 100 (and the spine) during surgery. Torques applied to the spine can stress the injury, cause pain for the patient, slow the healing process, and other undesirable effects. A spine stabilization system that does not exert torque on the vertebrae may require fewer tools, may simplify the surgery, reduce surgery time, and other benefits.

In some embodiments, after rod 10 is seated in collar 30, the surgeon may seat rod 10 in other collars 30 before advancing resilient inserts 50. Seating rod 10 in multiple channels in multiple collars 30 before advancing any of the resilient inserts 50 allows a surgeon to verify placement or positioning of rod 10, collars 30 and resilient inserts 50. The surgeon may remove rod 10 from channels 40, move rod 10, bend rod 10, or make other adjustments or changes to spine stabilization system 100.

In some embodiments, after rod 10 is seated in collar 30, additional fluoroscopic confirmation of rod positioning may be obtained. With the rod satisfactorily positioned, the rod may be secured in place with resilient inserts 50. Resilient insert 50 may be positioned in a first collar 30 and then second collar 30. After resilient insert 50 is successfully positioned in arms 34 of collar 30, pin 60 may be inserted in central passage 52 of resilient insert 50. After pin 60 is positioned in resilient insert 50, the tool may be removed from the patient.

Pin 60 may be removed from resilient insert 50 to allow a surgeon to remove resilient insert 50. Resilient insert 50 may be removed to allow access to rod 10. Rod 10 may be removed from collar 30. When rod 10 is removed from collar 30, a surgeon may access head 22 of bone fastener 20. A driver may be coupled to bone fastener 20 and bone fastener 20 and/or collar 30 may be removed from the patient.

Embodiments of spine stabilization system 100 may be used to stabilize two or more vertebral levels (i.e., at least three adjacent vertebrae). In one embodiment, an incision may be made in the skin between the outermost vertebrae to be stabilized. A first bone fastener assembly may be coupled to a first sleeve. The first bone fastener may be threaded into a first pedicle at a target location such that the first sleeve extends above the body surface. The first sleeve may rotate about the head of the first bone fastener. A tissue plane may be created between a channel opening in the first sleeve and a target location at a second pedicle. In one embodiment, the second pedicle may be adjacent to the first pedicle. A second bone fastener assembly may be coupled to a second sleeve and threaded into the second pedicle through the incision. Another tissue plane may be created between the first sleeve or the second sleeve and a target location in a third pedicle. The third pedicle may be adjacent to the first pedicle and/or the second pedicle. A third bone fastener assembly may be coupled to a third sleeve and threaded into the third pedicle through the incision. In one embodiment of a method for a two-level spinal stabilization procedure, an incision may be made above a target location in a middle pedicle. A first bone fastener may be anchored to the middle pedicle. After the first bone fastener is secured, second and third bone fasteners may be coupled to outer pedicles as desired by pulling and/or stretching tissue surrounding the incision to allow access to the outer pedicles.

In some embodiments, spinal stabilization system 100 may be inserted using an invasive procedure. Since insertion of spinal stabilization system 100 in an invasive procedure may be visualized, cannulated components, such as bone fasteners 20 or inserts 50 and/or instruments (e.g., sleeves) may not be needed for the invasive (i.e., open) procedure. Thus, bone fastener 20 used in an invasive procedure may differ from bone fastener 20 used in a minimally invasive procedure.

In some embodiments, tools used in an invasive procedure may be similar to tools used in a minimally invasive procedure. In some embodiments, methods of installing spinal stabilization system 100 in an invasive procedure may be similar to methods of installing spinal stabilization system 100 in a minimally invasive procedure.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as the presently preferred embodiments. Elements and materials may be substituted for those illustrated and described herein, parts and processes may be reversed, and certain features of the disclosure may be utilized independently, all as would be apparent to one skilled in the art after having the benefit of this description of the disclosure. Changes may be made in the elements described herein without departing from the spirit and scope of the disclosure as described in the following claims.

What is claimed is:

1. An apparatus for securing a rod to a bone fastener, comprising:
   a collar comprising:
   a first end comprising:
   two arms, wherein each arm comprises a recessed portion on an inner surface; and
   a channel defined by the two arms and having a geometric configuration that accommodates the rod; and
   a second end comprising an opening opposite the first end and running at least partially from the second end of the collar to the first end of the collar to form a cavity;
   a resilient insert comprising:
   a central passage centered about the longitudinal axis of the resilient insert and running the length of the resilient insert;
   a ridge configured for engagement with the recessed portions of the collar; and
   a slot connected to the central passage and running the length of the resilient insert;
   wherein the resilient insert has an outer diameter greater than the width of the channel of the collar when the resilient insert is in a neutral state;
   wherein the slot is configured to allow the outer diameter of the resilient insert to decrease such that the resilient insert is insertable entirely inside the channel of the collar, allowing the ridge of the resilient insert to engage the recessed portions of the two arms to inhibit passage of the resilient insert out of the recessed portions of the collar; and a pin comprising:
- a central core for insertion into the central passage of the resilient insert; and
- a radial extension having a selected thickness for insertion into the slot of the resilient insert to inhibit the outer diameter of the resilient insert from decreasing.

2. The apparatus of claim 1, wherein a portion of the radial extension of the pin has a selected thickness greater than the width of the slot.

3. The apparatus of claim 2, wherein the radial extension on the pin has a tapered thickness, wherein the radial extension is configured to increase the outer diameter of the resilient insert to a diameter greater than the outer diameter of the resilient insert in a neutral state.

4. The apparatus of claim 3, wherein the width of the slot, the outer diameter of the resilient insert, and the width of the channel are configured to create a cold weld between the pin, the resilient insert and the two arms when the resilient insert is inserted in the channel of the collar and the pin is inserted in the resilient insert.

5. The apparatus of claim 1, wherein the recessed portions have a radius of curvature.

6. The apparatus of claim 5, wherein the resilient insert is configured to exert a downward force on the resilient insert for increased friction contact with a rod when the resilient insert is positioned in the recessed portions of the two arms.

7. The apparatus of claim 6, wherein a head of a bone fastener is positionable into the cavity, wherein the width of the slot, the outer diameter of the resilient insert, and the width of the channel are configured to create a cold weld between the resilient insert, a rod positioned in the channel, and the head of a bone fastener positioned in the cavity when the resilient insert is inserted in the channel of the collar and the pin is inserted in the resilient insert.

* * * * *